US008598132B2

(12) United States Patent
Pérez Salas et al.

(10) Patent No.: US 8,598,132 B2
(45) Date of Patent: Dec. 3, 2013

(54) GLYCOSYLATED INDOLOCARBAZOLES, METHOD FOR OBTAINING SAME AND USES THEREOF

(75) Inventors: Aaroa Pérez Salas, Oviedo (ES); César Sánchez Reillo, Oviedo (ES); Alfredo Fernández Braña, Oviedo (ES); Carmen Méndez Fernández, Oviedo (ES); Jose Antonio Salas Fernández, Oviedo (ES); Francisco Morís Varas, Oviedo (ES)

(73) Assignees: Universidad de Oviedo, Oviedo (ES); Entrechem, S.L., Oviedo (ES)

( * ) Notice: Subject to any disclaimer, the term of this patent is extended or adjusted under 35 U.S.C. 154(b) by 160 days.

(21) Appl. No.: 12/989,778

(22) PCT Filed: Apr. 6, 2009

(86) PCT No.: PCT/ES2009/070092
§ 371 (c)(1),
(2), (4) Date: Feb. 14, 2011

(87) PCT Pub. No.: WO2009/125042
PCT Pub. Date: Oct. 15, 2009

(65) Prior Publication Data
US 2011/0136753 A1    Jun. 9, 2011

(30) Foreign Application Priority Data
Apr. 8, 2008 (ES) .................................. 200801077

(51) Int. Cl.
| A61K 31/70 | (2006.01) |
| C07H 17/02 | (2006.01) |
| C07H 21/00 | (2006.01) |
| C12P 1/00 | (2006.01) |
| C12P 19/28 | (2006.01) |
| C12N 1/22 | (2006.01) |

(52) U.S. Cl.
USPC ............. 514/43; 536/17.4; 536/22.1; 435/41; 435/85; 435/252.1; 435/887

(58) Field of Classification Search
USPC ........ 536/18.7, 17.4, 22.1; 435/41, 85, 252.1, 435/887; 514/43
See application file for complete search history.

(56) References Cited

U.S. PATENT DOCUMENTS
2008/0004326 A1    1/2008  Sanchez Reillo et al.

FOREIGN PATENT DOCUMENTS
| AU | 200071681 B2 | 11/2000 |
| EP | 0769555 A1 | 4/1997 |
| EP | 1101770 A1 | 5/2001 |
| JP | 4273891 A1 | 9/1992 |
| WO | 91/09034 A1 | 6/1991 |
| WO | 02/30941 A2 | 4/2002 |
| WO | 03/033706 A1 | 4/2003 |

OTHER PUBLICATIONS

Sanchez, Cesar, The Biosynthetic Gene Cluster for the Antitumor Rebeccamycin: Characterization and Generation of Indolocarbazole Derivatives, Chemistry & Biology, Apr. 2002, pp. 519-531, vol. 9.

Primary Examiner — Elli Peselev
(74) Attorney, Agent, or Firm — Tristan A. Fuierer; Moore & Van Allen, PLLC

(57) ABSTRACT

Glycosylated indolocarbazoles, method for obtaining same and uses thereof. This invention relates to rebeccamycin and staurosporine derivatives obtained by fermentation of recombinant bacterial strains. The invention also relates to the methods used to obtain the recombinant strains and the production of rebeccamycin and staurosporine derivatives. The invention also relates to bacterial strains that are of use for the production of rebeccamycin and staurosporine derivatives. Lastly, the rebeccamycin and staurosporine derivatives described herein are applicable to the field of human health, specifically for manufacturing drugs that are of use in the treatment of tumour, neurological and inflammatory diseases.

18 Claims, 5 Drawing Sheets

STP RBM

| Cpd | General Formula | R₁ | R₂ | R₃ | R₄ | R₅ | R₆ | R₇ | R₈ | R₉ | R₁₀ | R₁₁ | R₁₂ |
|------|------|----|----|----|----|----|----|----|----|----|----|----|----|
| (III) | (I) | H | H | H | H | H | OH | H | OH | OH | H | H | Me |
| (IV) | (I) | H | H | H | H | H | H | H | OH | OH | H | H | Me |
| (V) | (I) | H | H | H | H | H | H | OH | H | OH | H | H | Me |
| (VI) | (I) | H | H | H | H | H | H | OH | H | H | OH | Me | H |
| (VII) | (II) | H | H | H | - | H | OH | H | OH | OH | H | - | - |
| (VIII) | (II) | H | H | H | - | H | H | H | OH | OH | H | - | - |
| (IX) | (II) | H | H | H | - | H | H | OH | H | OH | H | - | - |
| (XII) | (X) | H | H | H | H | H | OH | H | OH | OH | H | H | Me |
| (XIII) | (X) | H | H | H | H | H | H | H | OH | OH | H | H | Me |
| (XIV) | (X) | H | H | H | H | H | H | OH | H | OH | H | H | Me |
| (XV) | (X) | H | H | H | H | H | H | OH | H | H | OH | Me | H |
| (XVI) | (XI) | H | H | H | - | H | OH | H | OH | OH | H | - | - |
| (XVII) | (XI) | H | H | H | - | H | H | H | OH | OH | H | - | - |
| (XVIII) | (XI) | H | H | H | - | H | H | OH | H | OH | H | - | - |

GLYCOSYLATED INDOLOCARBAZOLES, METHOD FOR OBTAINING SAME AND USES THEREOF

CROSS-REFERENCE TO RELATED APPLICATIONS

This application is filed under the provisions of 35 U.S.C. §371 and claims the priority of International Patent Application No. PCT/ES2009/070092 filed on 6 Apr. 2009 entitled "Glycosylated Indolecarbazoles, Method for Obtaining Same and Uses Thereof" in the name of Aaroa Perez Salas, et al., which claims priority to Spanish Patent Application No. P200801077 filed on 8 Apr. 2008, both of which are hereby incorporated by reference herein in their entireties.

The invention relates to the pharmaceutical field and specifically relates to compounds applicable in oncology, with chemical structure derived from indolocarbazole, and which is obtained by the fermentation of microorganisms.

STATE OF THE ART

Over 120 natural products of indolocarbazole-type have been isolated from bacteria, fungi and marine invertebrates (Studies in *Natural Product Chemistry*, Elsevier, Amsterdam, vol. 12, pp. 365-409, 1993; *Chem. Rev.* 2002, 102: 4303-4427; *Nat. Prod. Rep.* 2006, 23, 1007-1045). Among these compounds of natural origin we can highlight staurosporine (STP, FIG. 1) and rebeccamycin (RBM), which are glycosylated indolocarbazoles produced by bacteria from the group of actinomycetes (U.S. Pat. No. 4,487,925; U.S. Pat. No. 4,552,842; *J. Antibiot.* 1977, 30, 275-282; *Tetrahedron Lett.* 1985, 26, 4011-4014; *J. Antibiot.* 1987, 40, 668-678; *Nat. Prod. Rep.* 2006, 23, 1007-1045). Furthermore, a high number of indocarbozole type derivatives have been obtained, including a number of indolocarbazole-type derivatives, including glycosylated indolocarbazoles, by chemical synthesis or semi-synthesis (*Studies in Natural Product Chemistry*, Elsevier, Amsterdam, vol. 12, pp. 365-409, 1993; *Chem. Rev.* 2002, 102: 4303-4427; *Eur. J. Med. Chem.* 2003, 38, 123-140; *Curr. Med. Chem. Anti-Cancer Agents* 2002, 2, 255-266; *Anti-Cancer Drug Design* 2000, 15, 43-52; *J. Med. Chem.* 2005, 48, 2600-2611; U.S. Pat. No. 4,785,085; EP0545195; EP0602597; WO9807433; WO9902532; WO9530682; U.S. Pat. No. 5,475,110; U.S. Pat. No. 5,468,872; U.S. Pat. No. 6,686,385; U.S. Pat. No. 6,610,727; U.S. Pat. No. 6,855,698).

Indolocarbazoles have a broad variety of biological activities of pharmaceutical interest, with antibacterial, antifungal, antiviral, hypotensive, antitumor and neuroprotector properties. For example, rebeccamycin (U.S. Pat. Nos. 4,487,925 and 4,552,842) and its water-soluble analog 6-(2-diethylaminoethyl)-rebeccamycin (U.S. Pat. No. 4,785,085) show anti-tumour activity. These biological activities may be the result of different action mechanisms, including the inhibition of protein kinases, the inhibition of DNA topoisomerases or intercalative binding to DNA (*Anti-Cancer Drug Design* 2000, 15, 43-52; *Curr. Med. Chem. Anti-Cancer Agents* 2002, 2, 255-266; *Eur. J. Med. Chem.* 2003, 38, 123-140; *Nat. Prod. Rep.* 2006, 23, 1007-1045). Several indolocarbazole derivatives have gone into clinical trials for the treatment of cancer or of certain neurological disease such as Parkinson's (*Nat. Prod. Rep.* 2005, 22: 162-195; *Nat. Prod. Rep.* 2006, 23, 1007-1045). Most of these derivatives are glycosides, which are generally more powerful that the corresponding agly-cones (*Eur. J. Med. Chem.* 2003, 38, 123-140; *J. Med. Chem.* 2005, 48, 2600-2611). In the glycosides, sugar can be bonded to indolocarbazole by a single N-glycosidic bond (as in the case of RBM, FIG. 1) or by two bonds, which consist of an N-glycosidic bond and an additional C—N bond (as in STP). Another relevant difference between the structures of RBM and STP are found in the pyrrol group, including an amide in RBM and an imide in STP. These differences are of great importance for the compound's action mechanism, since RBM is an inhibitor of the DNA topoisomerase I, whilst STP is a protein kinase inhibitor.

There is currently a great need for new anti-tumour agents, with improved activity, with less undesirable secondary effects and with greater selectivity, in comparison with the drugs currently in use. The pharmaceutical industry has traditionally developed new drugs through two fundamental channels: (1) the search for new natural products, and (2) the synthesis and/or chemical modification of certain compounds. These methods continue to be useful, but they usually require very considerable investments in resources (time, money, energy), as it is normally necessary to analyse thousands of products to find a new promising compound. The development of recombinant DNA technology has opened an interesting field of research to generate new bioactive compounds with the manipulation of genes involved in the biosynthesis of anti-tumour agents, mainly bacteria from the group of actinomycetes (*Trends Biotechnol.* 2001, 19, 449-456; *J. Mol. Microbiol. Biotechnol.* 2005, 9, 77-85; *Curr. Opin. Drug Discov. Devel.* 2005, 8, 748-756; *J. Ind. Microbiol. Biotechnol.* 2006, 33, 560-568; *Curr. Opin. Microbiol.* 2006, 9, 252-260). These techniques can also be used to improve the production of already known natural compounds, since the natural strains usually produce low concentrations of the metabolite of interest.

Genetic manipulation of microorganisms has already been used to obtain several dozen indolocarbazole-type derivatives (ES2255331-A12006; *Chem. Biol.* 2002, 9, 519-531; *Biosci. Biotechnol. Biochem.* 2003, 67, 127-138; *Proc. Natl. Acad. Sci. USA* 2005, 102, 461-466; *Mol. Microbiol.* 2005, 58, 17-27). At least some of these derivatives have anti-tumour activity (*Proc. Natl. Acad. Sci. USA* 2005, 102, 461-466). The biosynthesis of glycosylated indolocarbazoles may be achieved by the expression of four genes for the formation of the aglycone, a gene which encodes a glycosyltransferase, and a variable number of genes which encode enzymes for sugar formation. The expression of an additional gene (staN) allows the production of STP analogs, with the sugar bound to the aglycone by two bonds (*Mol. Microbiol.* 2005, 58, 17-27). The expression of all these genes in a suitable host cell gives rise to a biosynthetic route such as, for example, that illustrated in FIG. 2.

DESCRIPTION OF THE INVENTION

The present invention provides new compounds derived from rebeccamycin and staurosporine, belonging to the family of glycosylated indolocarbazoles. The present invention also provides new bacterial strains that produce glycosylated indolocarbazoles. These bacterial strains are obtained by the introduction of certain additional nucleic acids in strains of *Streptomyces* spp. that are not indolocarbazole-producers, in particular *Streptomyces albus*. Said nucleic acids are of two types. The first type consists of nucleic acids which encode enzymatic activities involved in the biosynthesis of Rebeccamycin and Staurosporine, and may be obtained from *Lechevalieria aerocolonigenes* ATCC39243, *Streptomyces long-isporoflavus* DSM10189 or of any other indolocarbazole-producing organism. The second type consists of nucleic acids which encode enzymatic activities involved in the biosynthesis of sugars that form part of the structure of various glycosides (glycosides such as RBM, STP, erythromycin, oleandomycin, urdamycin, or others), and may be obtained from *Lechevalieria aerocolonigenes* ATCC39243, *Streptomyces longisporoflavus* DSM10189, *Saccharopolyspora erythraea* NRRL2338, *Streptomyces antibioticus* ATCC11891, *Streptomyces fradiae* Tü2717 or any glycoside producing organism.

Nucleic acids can be introduced in *Streptomyces* spp. by transformation of protoplasts, conjugation, or other known methods (such as those described in Practical *Streptomyces* genetics, The John Innes Foundation, Norwich, Great Britain, 2000), so that the nucleic acids are replicable in the organism, either in the form of extra-chromosomal element or integrated in the organism's chromosome.

The bacterial strains of this invention can be cultivated in any suitable medium, in conditions that allow their growth, as described in *J. Nat. Prod.* 2002, 65, 779-782; *Chembiochem.* 2004, 5, 1181-1187. After several days' incubation these cultures contain high cell levels (mycelium), together with a mixture of compounds, including indolocarbazole derivatives. Next, the cultures undergo processes to separate the liquid phase (supernatant) and a solid phase (mycelium). Then the two phases undergo, separately, various methods that may include extraction with various organic solvents and different types of chromatographies (such as HPLC, high performance liquid chromatography, in order to obtain the indolocarbazole derivatives in the form of pure compounds. The indolocarbazole derivatives have anti-tumour and antibiotic activity, protein kinase inhibitor activity, DNA topoisomerase inhibitor activity, and others.

Likewise, the present invention provides compounds characterized in that they have the following formulas (I) and (II):

(I)

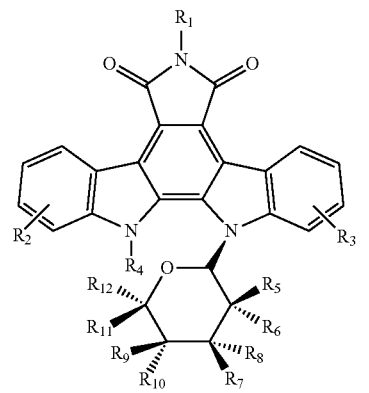

(II)

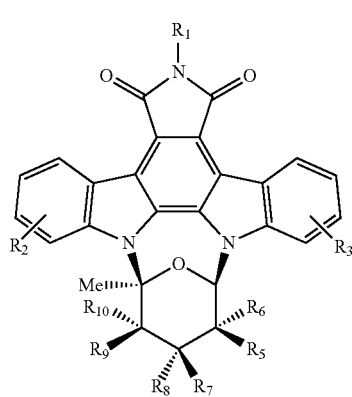

where $R_1$, $R_2$, $R_3$ and $R_4$ are, each one and independently, hydrogen or a protector group. The protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof, $R_5$, $R_6$, $R_7$, $R_8$, $R_9$ and $R_{10}$ are, each one and independently, hydrogen, hydroxyl (—OH) or an —$OR_{13}$ group, where $R_{13}$ is a protector group according to the previous definition, $R_{11}$ and $R_{12}$ are each one and independently hydrogen, methyl (—$CH_3$), a hydroxymethyl group (—$CH_2OH$) or a group —$CH_2OR_{14}$, where $R_{14}$ is a protector group according to the previous definition.

In particular, the present invention provides, among others, the compounds with the following formulas (III), (IV), (V), (VI), (VII), (VIII) and (IX):

(III)

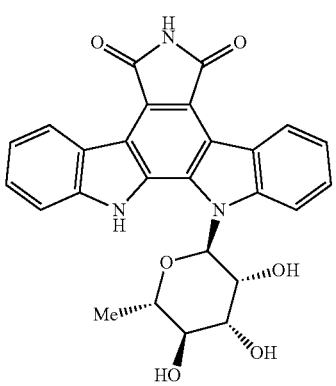

(IV)

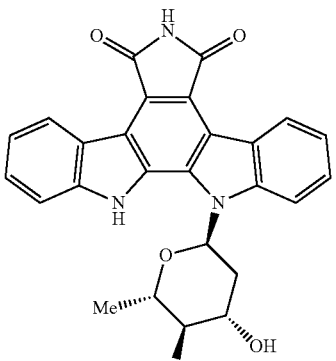

(V)

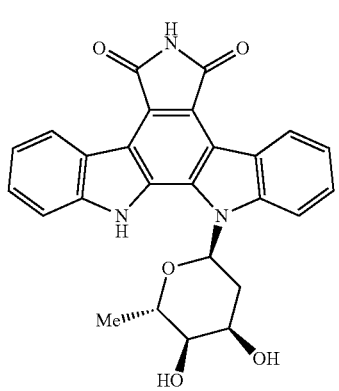

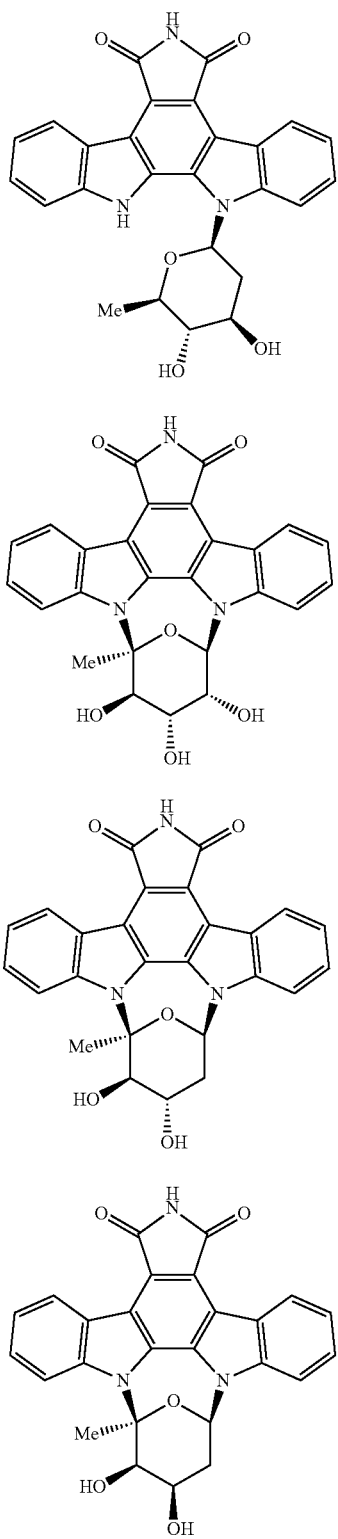

The compound of formula (III) is new as a similar glycosylated indolocarbarzole was previously described but the stereochemistry thereof is not defined in the glycoside bond, which in the case of this invention is of β configuration (Tetrahedron Lett. 2004, 45, 1095-1098).

Likewise, the present invention provides new uses for the compounds characterized in that they have formulas (X) and (XI):

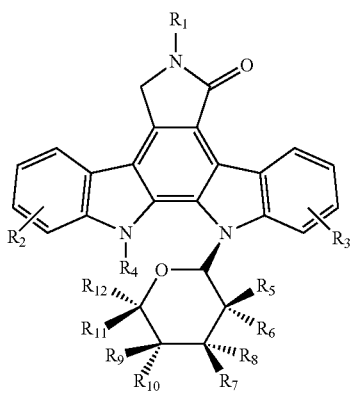

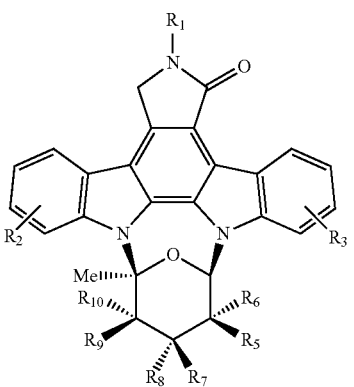

where $R_1$, $R_2$, $R_3$ and $R_4$ are, each one and independently, hydrogen or a protector group. The protector group may consist of an alkyl group, a cycloalkyl group, a heterocyclic cycloalkyl group, a hydroxyalkyl group, a halogenated alkyl group, an alkoxyalkyl group, an alkenyl group, an alkynyl group, an aryl group, a heterocyclic aryl group, an alkylaryl group, an ester group, a carbonate group, a carboxylic acid group, an aldehyde group, a ketone group, a urethane group, a silyl group, a sulfoxide group or a combination thereof, $R_5$, $R_6$, $R_7$, $R_8$, $R_9$ and $R_{10}$ are, each one and independently, hydrogen, hydroxyl (—OH) or an —$OR_{13}$ group, where $R_{13}$ is a protector group according to the previous definition, $R_{11}$ and $R_{12}$ are each one and independently hydrogen, methyl (—$CH_3$), a hydroxymethyl group (—$CH_2OH$) or a group —$CH_2OR_{14}$, where $R_{14}$ is a protector group according to the previous definition.

In particular, the present invention provides new uses for, among others, the compounds with formulas (XII), (XIII), (XIV), (XV), (XVI), (XVII) and (XVIII):

(XII)
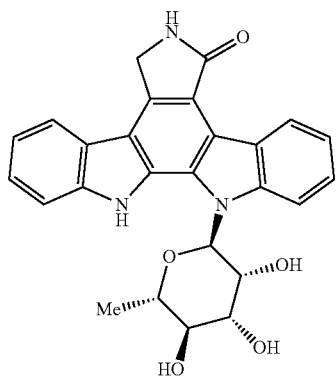

(XIII)
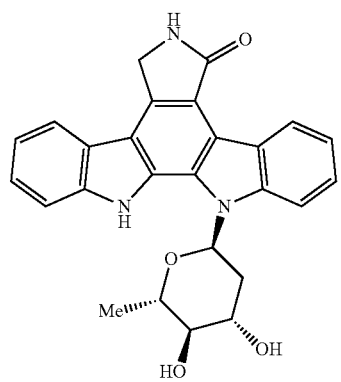

(XIV)
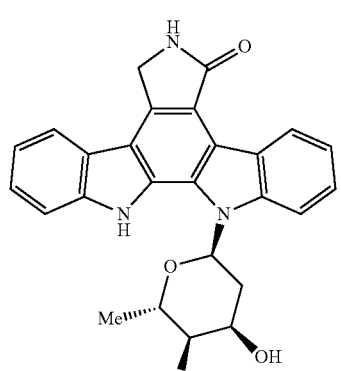

(XV)
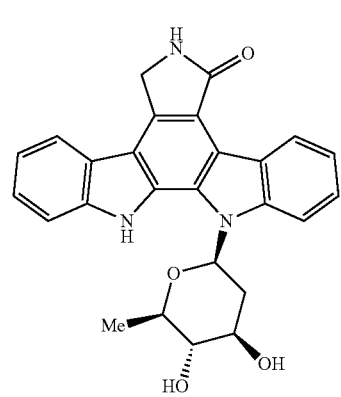

(XVI)
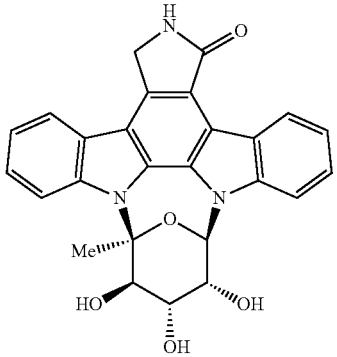

(XVII)
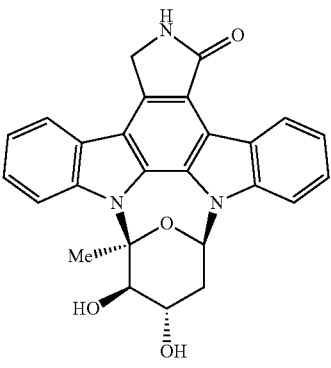

(XVIII)
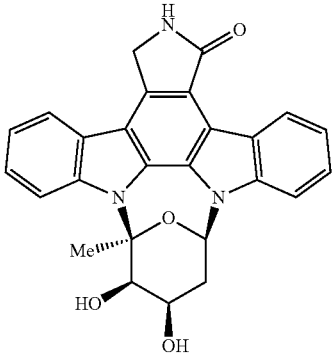

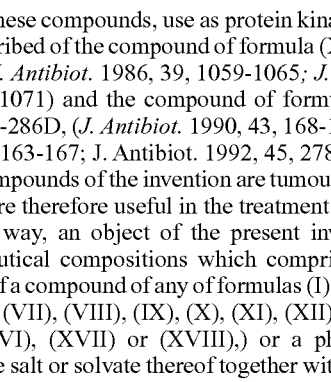

Of all these compounds, use as protein kinase C(PKC) has been described of the compound of formula (XII), also called K252d, (*J. Antibiot.* 1986, 39, 1059-1065; *J. Antibiot.* 1986, 39, 1066-1071) and the compound of formula (XIV), also called RK-286D, (*J. Antibiot.* 1990, 43, 168-173; J. Antibiot. 1990, 43, 163-167; J. Antibiot. 1992, 45, 278-279).

The compounds of the invention are tumour growth inhibitors and are therefore useful in the treatment of cancer.

In this way, an object of the present invention are the pharmaceutical compositions which comprise an effective quantity of a compound of any of formulas (I), (II), (III), (IV), (V), (VI), (VII), (VIII), (IX), (X), (XI), (XII), (XIII), (XIV), (XV), (XVI), (XVII) or (XVIII),) or a pharmaceutically acceptable salt or solvate thereof together with a pharmaceutically acceptable excipient.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, in the manufacturing of a drug.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, to inhibit tumour growth.

As used here "inhibit" means to reduce, make slower, or stop. Therefore, a compound of this invention may reduce, make slower or stop the growth of a tumour cell. As used here, "growth" means increase in size, or proliferation, or both. Therefore, a compound of this invention may inhibit the increase in size of a tumour cell and/or may prevent the tumour cell from dividing and increase the number of tumour cells. A "tumour cell" is a cell that constitutes a neoplasm (new growth), which may be cancerous (malignant) or non-cancerous (benign). A cancerous tumour cell may invade the normal tissue surrounding it and the blood/lymphatic vessels and form metastasis in tissue far from the original tumour. In contrast, a non-cancerous tumour cell may grow and compress the adjacent normal tissues but it cannot invade normal tissues and blood/lymphatic vessels and neither can it form metastasis in tissues far from the original tumour.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, to treat cancer.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, in the manufacturing of a drug with anti-tumour activity.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, in the manufacturing of a drug for the treatment of cancer.

A further object of the present invention is a method of treatment of a subject, including a human being, diagnosed with cancer, consisting of treating said mammal with a therapeutically effective quantity of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof.

As used here, a "subject" may include pets (for example, cats, dogs, etc.), farm animals (for example, cows, horses, pigs, sheep, goats, etc.), laboratory animals (for example, mice, rabbits, guinea pigs, etc.) and birds. Preferably, the subject is a mammal such as a primate and, with greater preference, a human being.

In general, an "effective quantity" of a compound is that quantity necessary to achieve the desired result. For example, the effective quantity of a compound of the present invention treats cancer by inhibiting the growth of cells that constitute the tumour, so that it prevents the invasion of normal tissues and blood/lymphatic vessels by the tumour cells and, therefore, prevents metastasis. Examples of cancers that can be treated include, but are not limited to, lung, colon, ovarian, prostate, testicular, melanoma, kidney, breast, central nervous system and leukaemia. The expression "pharmaceutically acceptable composition" consists of a biologically suitable material, i.e. that the material can be administered to the subject without causing him/her/it substantially harmful biological effects.

The doses or quantities of the compounds of the invention must be sufficiently large to produce the desired effect. However, the dose must not be as large as to cause adverse secondary effects, for example unwanted cross reactions, ana-phylactic reactions and such like. Generally, the dose will vary with age, condition, sex and degree of the subject's disease and can be determined by any person skilled in the art. The dose can be adjusted by each doctor, based on the clinical condition of the subject involved. The dose, dosage regime and administration route may vary.

A further object of the present invention is the use of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof, in the manufacturing of a drug for the treatment of neurological diseases.

A further object of the present invention is a method of treatment of a subject, including a human being, diagnosed with a neurological disease, consisting of treating said subject with a therapeutically effective quantity of a compound of any of formulas (I), (II), (III), (IV), (V), (VI), (VII), (VIII), (IX), (X), (XI), (XII), (XIII), (XIV), (XV), (XVI), (XVII) or (XVIII), or a pharmaceutically acceptable salt or solvate thereof. The subject may be a mammal, preferably a human being, and the compound may be, among other routes, administered parenterally.

Examples of neurological diseases that may be treated include, but are not limited to, neurodegenerative diseases such as Parkinson's, Alzheimer's, and Huntington's disease.

The compounds of the invention may be useful for research in biochemical or cellular biology. For example, the compounds may be effective to inhibit the activity of DNA topoisomerases and several protein kinases in in vitro cultures of several cell types. Examples of DNA topoisomerases which may be inhibited by the compounds of the invention include topoisomerase I, topoisomerase II, gyrase and others. Examples of protein kinases which may be inhibited by the compounds of the invention include AurA, AurB, Chk1, Dyrk1a, Ftl3, FGFR1, HGK, Ikkb, Jak2, KDR, SYK, and others.

Any of the compounds of the invention can be used therapeutically forming part of an acceptable pharmaceutical composition. Any person skilled in the art can create acceptable pharmaceutical compositions, which may consist of sterile solutions in water, saline solutions or solutions buffered to physiological pH. Any of the compounds of the invention may be prepared in the form of pharmaceutical composition. The pharmaceutical compositions may include various carrier agents, thickeners, buffers, preservatives, surfactants, and others, in addition to the compound of the invention. The pharmaceutical compositions may further include active ingredients such as antimicrobial agents, anti-inflammatory agents, anaesthetic agents, etc.

The compounds of the invention may be administered to the subject in several different ways, depending on whether one wants the treatment to be local or systemic, and depending on the area to be treated. Thus, for example, a compound of the present invention may be administered in the form of ophthalmic solution, for application on the eye surface. Furthermore, a compound may be administered to a subject by vaginal, rectal, intranasal, oral, by inhalation, or by parenteral route, whether intradermal, subcutaneous, intramuscular, intraperitoneal, intrarectal, intra-arterial, intralymphatic, intravenous, intrathecal and intratracheal. Parenteral administration, if used, is generally performed by injection. The solutions for injection can be prepared in various ways, such as solutions or liquid suspensions, solid forms suitable for being dissolved or placed in suspension before the injection, or as emulsions. Other forms of parenteral administration use systems of slow or sustained release, so that a constant dose is achieved (see, for example, U.S. Pat. No. 3,710,795). The preparations for parenteral administration include sterile aqueous or non-aqueous solutions, suspensions, and emulsions, and they may also contain buffers and diluent additives and others. Examples of non-aqueous solvents are: propylene glycol, polyethylene glycol, vegetable oils such as olive oil, and organic esters for injection such as ethyl oleate. Examples of aqueous solvents are: water, alcohol-aqueous solutions, emulsions or suspensions, including saline and buffer solutions. Examples of parenteral vehicles are: sodium chloride solution, Ringer's dextrose, sodium chloride and dextrose, etc. Preservatives and other additives may also be present, such as, for example, antimicrobial agents, anti-oxidants, chelating agents, inert gases, etc. The formulations for topical administration may include creams, lotions, gels, drops, suppositories, sprays, liquids and powders. Certain conventional pharmaceutical carriers, aqueous bases, oily bases or, in powder, thickeners, etc. may also be necessary. The compositions for oral administration may include powders or granules, suspensions or solutions in water or non-aqueous medium, capsules or tablets. It may be desirable to include thickening, flavouring, diluent, emulsifying, dispersant agents, etc.

For the purposes of the present invention and its description rebeccamycin or staurosporine "derivative" must be interpreted as a compound coated by any of formulas (I), (II), (X) or (XI). Likewise, the term "prodrug" must be interpreted for the purposes of the present invention and description thereof, as any compound that releases, when circulating in the blood or entering the cell, rebeccamycin, staurosporine or a derivative, in accordance with any of formulas (I), (II), (X) or (XI), thereof.

EXPLANATION OF A PREFERRED EMBODIMENT

Figure 1:
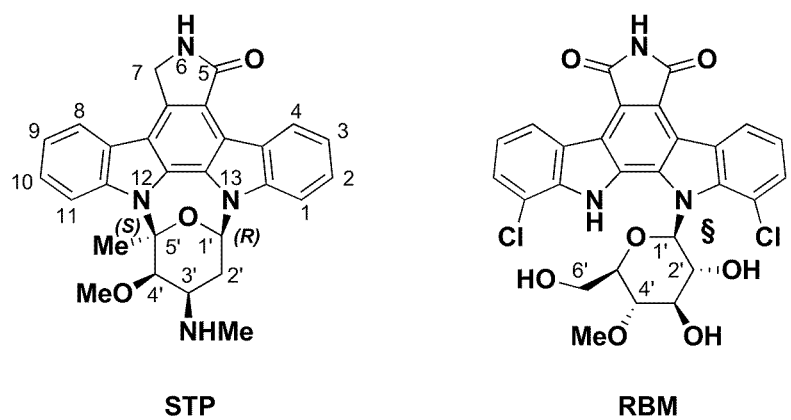
FIG. 1. Chemical structure of staurosporine (STP) and rebeccamycin (RBM).
Figure 2:
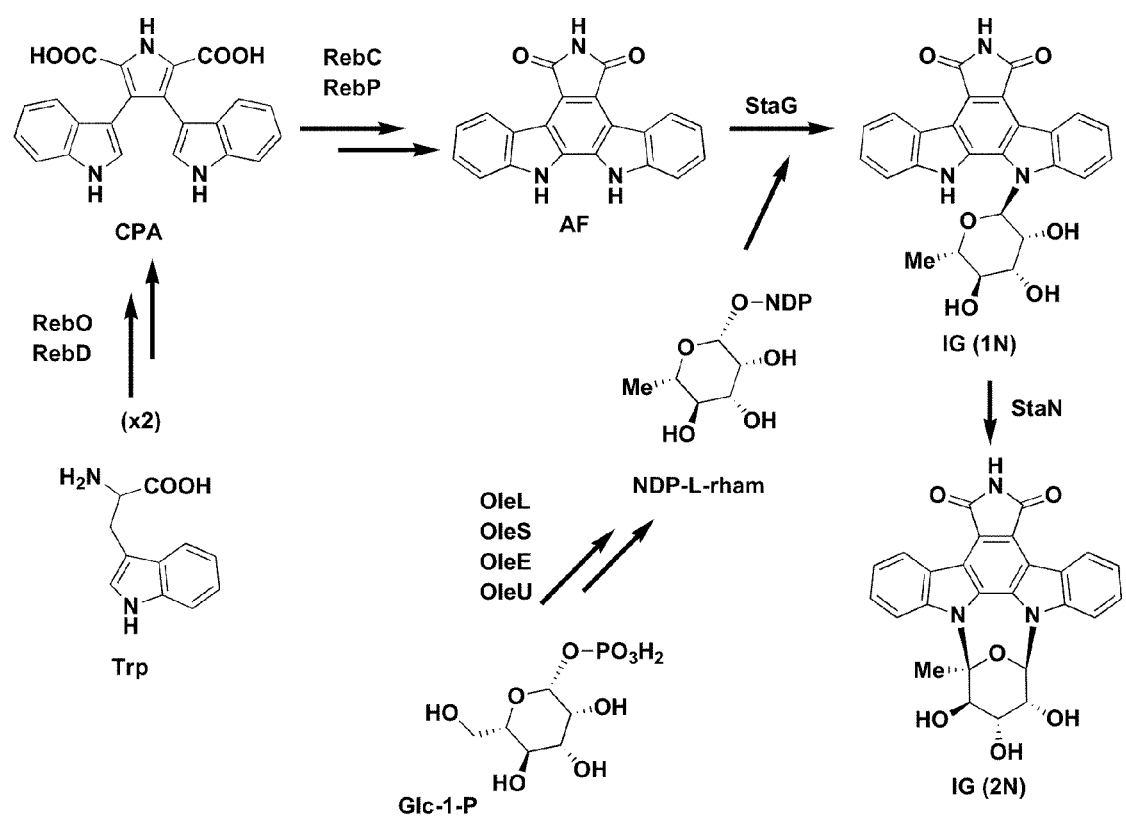
FIG. 2. Biosynthesis of a glycosylated indolocarbazole. Abbreviations: Trp (tryptophan), CPA (chromopyrrollic acid), AF (arcyriaflavin A), NDP-L-rham (nucleosidyl diphosphate [NDP]-L-rhamnose), Glc-1-P (glucose 1-phosphate), IG(1N) (glycosylated indolocarbazole with sugar bound by a single bond), IG(2N) (glycosylated indolocarbazole with sugar bound by two bonds). RebO, RebD, RebC and RebP are enzymes participating in the biosynthesis of rebeccamycin. StaG and StaN are enzymes of the staurosporine formation route. OleL, OleS, OleE and OleU are enzymes involved in the formation of oleandomycin sugars.
Figure 3:
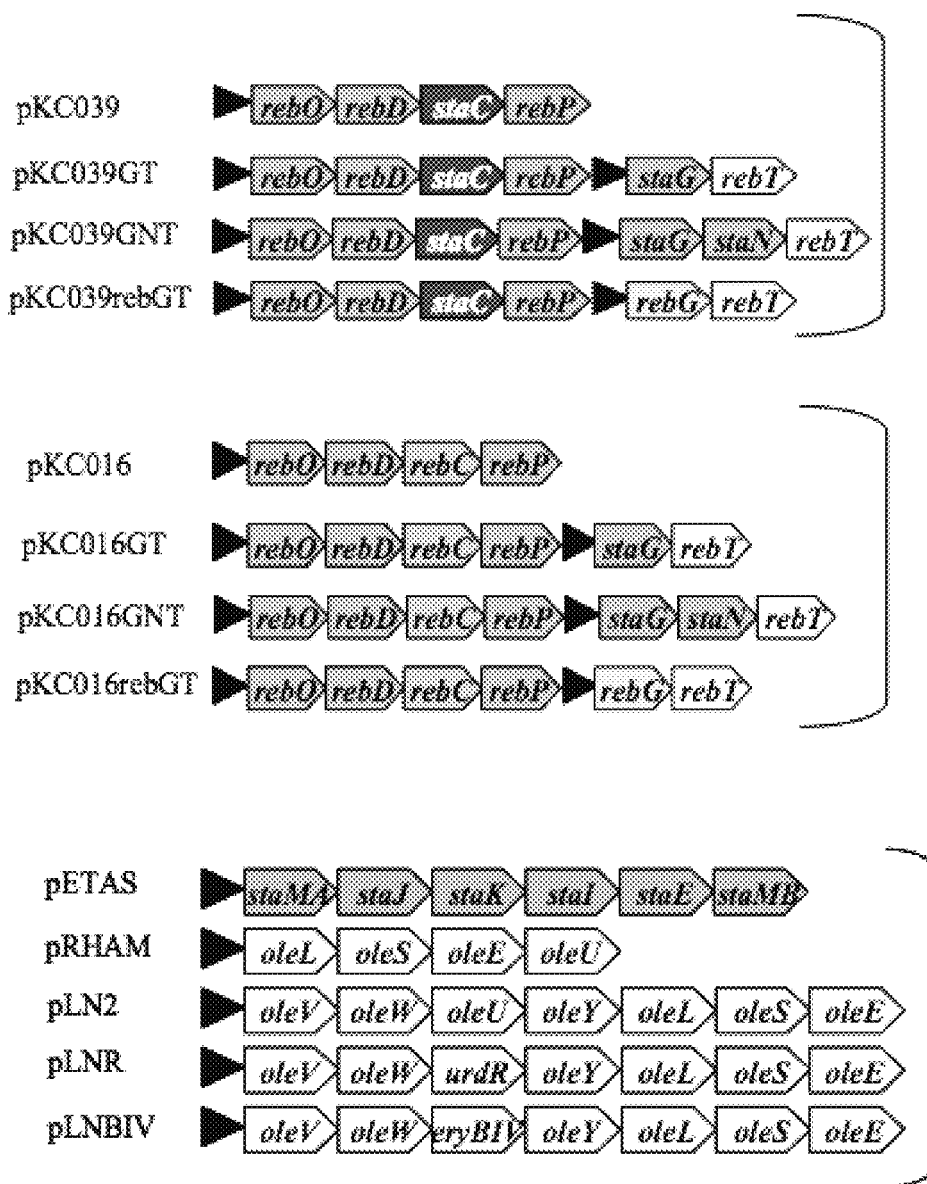
FIG. 3. Plasmids used, showing their genetic composition. The black triangles represent the promoter $P^*_{ermE}$.

For a better understanding of the present invention, the following examples are given, described in detail, which must be understood without limiting the scope of the invention.

The following examples use DNA manipulation techniques well known in the state of the art, such as those described by Sambrook et al. (Molecular Cloning, a Laboratory Manual, 2nd ed., Cold Spring Harbor Laboratory Press, New York, 1989), and by Kieser et al. (Practical *Streptomyces* genetics, The John Innes Foundation, Norwich, Great Britain, 2000).

EXAMPLE 1

Obtainment of the Bacterial Strains *Streptomyces albus* 16GNT(pRHAM), *Streptomyces albus* 16GNT(pLNBIV), *Streptomyces albus* 16GNT(pLN2) and *Streptomyces albus* 16GNT(pLNR)

In first place, plasmid pKC16GNT was constructed, which encodes four enzymes for the formation of the aglycone indolocarbazole (RebO, RebD, RebC and RebP), a glycosyltransferase for the formation of the N-glycosidic bond (StaG), an oxygenase of type P-450 for the formation of the second aglycone-sugar bond (StaN), and a protein which gives resistance to rebeccamycin (RebT). For this, a DNA fragment including staG and staN was obtained por PCR (polymerase chain reaction) using total DNA from *Streptomyces longisporoflavus* DSM10189 and the oligonucleotides CS043 (5'-TATATTACTAGTCGCGGAGGCGACGTTGAC-3') and STAN2 (5'-TATCTAGAGTCAGTTCAGTACGGCGGGC-3'). This fragment of DNA was cloned as a SpeI-XbaI fragment in the same sites of LITMUS 28 (New England BioLabs), generating plasmid pLGTFstaN. Next, plasmid pKC16GNT was obtained by tandem cloning, at the XbaI site of pKC016 (*Proc. Natl. Acad. Sci. USA* 2005, 102, 461-466), of three fragments of DNA containing: the promoter ermE*p (isolated as a HindIII-BamHI fragment from plasmid pEM4 [*Mol. Microbiol.* 1998, 28, 1177-1185]), the pLGTFstaN insert (containing staG and staN) and the rebT gene (obtained by PCR as described in *Proc. Natl. Acad. Sci. USA* 2005, 102, 461-466), respectively.

Next, said plasmid pKC16GNT was introduced in *Streptomyces albus* J1074 (*J. Gene. Microbiol.* 1980, 116, 323-334), generating the strain *Streptomyces albus* 16GNT. The introduction of the plasmid was performed by transformation of protoplasts, following standard procedures (Kieser et al., Practical *Streptomyces genetics*, The John Innes Foundation, Norwich, Great Britain, 2000). From the strain *Streptomyces albus* 16GNT the bacterial strains *Streptomyces albus* 16GNT(pRHAM), *Streptomyces albus* 16GNT(pLNBIV), *Streptomyces albus* 16GNT(pLN2) and *Streptomyces albus* 16GNT(pLNR) were obtained by the introduction, separately, of each one of the following plasmids: pRHAM, pLNBIV, pLN2 and pLNR, respectively. These four plasmids have been previously described (*J. Mol. Microbiol. Biotechnol.* 2000, 2, 271-276; *Chem. Biol.* 2002, 9, 721-729; *J. Nat. Prod.* 2002, 65, 1685-1689), and encode enzymes for the biosynthesis of the following sugars (in the form of NDP or nucleosydil diphosphate): L-rhamnose, L-digitoxose, L-olivose and D-olivose, respectively.

The strains *Streptomyces albus* 16GNT(pRHAM) *Streptomyces albus* 16GNT(pLNBIV), *Streptomyces albus* 16GNT (pLN2) and *Streptomyces albus* 16GNT(pLNR) were deposited on Mar. 14, 2008 in the Colección Española de Cultivos Tipo (CECT) (Spanish Type Culture Collection), University of Valencia, Campus de Burjassot, 46100 Burjassot (Valencia, Spain) with access numbers CECT 7388, CECT 7389, CECT 7390 and CECT 7391, respectively.

EXAMPLE 2

Production of the Compounds of Formula (III), (IV), (V), (VI), (VII), (VIII), (IX), and the Compounds of Formula (XII), (XIII), (XIV), (XV), (XVI) and (XVIII)

The obtainment of the new indolocarbazole derivatives was carried out with preparative HPLC (high performance liquid chromatography). For the obtainment of the compounds of formulas (III), (IV), (V), (VI), (VII), (VIII) and (IX), the strains *Streptomyces albus* 16GNT(pRHAM) *Streptomyces albus* 16GNT(pLNBIV), *Streptomyces albus* 16GNT(pLN2) and *Streptomyces albus* 16GNT(pLNR) were first cultured in 50 ml of TSB with the suitable resistance marker and they were left to grow for 24 hours at 30° C. and at 250 rpm. After 24 hours, from the pre-inoculation, they were inoculated at 2.5% flasks with 400 ml of liquid R5A medium, as previously described (*Mol. Microbiol.* 2005, 58, 17-27).

In the production step 8×2 liter Erlenmeyer flasks were used, each one containing 400 ml of medium, which were incubated at 30° C. and 250 rpm, for 4-5 days. The cultures were centrifuged at 12,000 rpm during 30 minutes. Most of these compounds are found both in the broth and the cells. The precipitates were extracted with acetone and the supernatants were filtered using a Mini Profil cartridge (1 μm) (Pall). The broth filtered is subject to an extraction in solid phase (SepPaK Vac C18, Waters). The retained compounds were eluted with a linear gradient of methanol and 0.1% TFA in water (0 to 100% methanol in 60 min, at 10 ml/min), collecting fractions every 5 minutes.

The extracts obtained were analysed by HPLC. It was performed using an Alliance chromatographic module coupled to a 2996 photodiode detector and to a ZQ4000 mass spectrometer (Waters-Micromass). The column used was a Symmetry C18 (2.1×150 mm, Waters) using acetonitrile and 0.1% trifluoroacetic acid in water as solvents. The elution began with 10% acetonitrile for 4 minutes, followed by a linear gradient until reaching 88% in minute 30, lastly 100% acetonitrile was pumped for 5 minutes, with a flow of 0.25 ml/min. performed by electrospray ionization in positive mode with a capillary voltage of 3 kV and cone voltages of 20, 60 and 100V. The wavelength at which the chromatograms were obtained was 290 nm for the compounds with staurosporine spectrum and 316 nm for the compounds with rebeccamycin spectrum.

After their analysis, those that contained the compounds sought were evaporated in the rotary evaporator, after addition of 10 ml of 0.1M pH 7 phosphate buffer to each one of them. The extracts, previously dissolved in a small volume of DMSO and acetone (50:50) were chromatographed in a μBondapak C18 radial compression cartridge (PrepPaK Cartridge, 25×100 mm, Waters), using, as mobile phase, mixtures of acetonitrile (or methanol) and 0.1% TFA in water at a flow of 10 ml/min and collecting the compounds of interest in multiple injections. In other purifications, an XTerra column was used (7.8×300 mm, Waters) and the same process was followed although working at 3 ml/min. The purified compound solutions were diluted with three volumes of water and underwent an extraction in solid phase to eliminate the acid from the mobile phase and concentrate the compounds. Lastly, they were freeze-dried for their conservation.

Figure 4A:
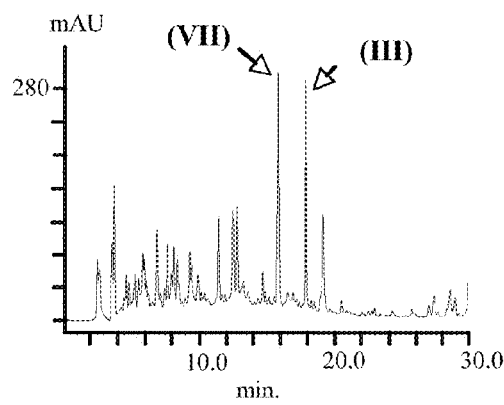
FIG. 4A, FIG. 4B, FIG. 4C, FIG. 4D. HPLC analysis of the cultures of the recombinant strains generated with plasmids that direct the synthesis of different deoxy-sugars: S. albus 16GNT(pRHAM) (FIG. 4A), S. albus 16GNT(pLN2) (FIG. 4B), S. albus 16GNT(pLNR) (FIG. 4C) and S. albus 16GNT(pLNBIV) (FIG. 4D). Peak guide: (VII): $N^{12}$-5'(S)—$N^{13}$-1'-(R)-L-rhamnosylarcyriaflavin [formula (VII)]; (III): $N^{13}$-1'-β-L-rhamnosylarcyriaflavin [formula (III)]; (VIII): $N^{12}$-5'(S)—$N^{13}$-1'-(R)-L-olivosylarcyriaflavin [formula (VIII)]; (IV): $N^{13}$-1'-β-L-olivosylarcyriaflavin [formula (IV)]; (VI): $N^{13}$-1'-β-D-olivosylarcyriaflavin [formula (VI)]; (V): $N^{13}$-1'-β-L-digitoxosylarcyriaflavin [formula (V)]; (IX): $N^{12}$-5'(S)—$N^{13}$-1'-(R)-L-digitoxosylarcyriaflavin [formula (IX)].
Figure 4B:
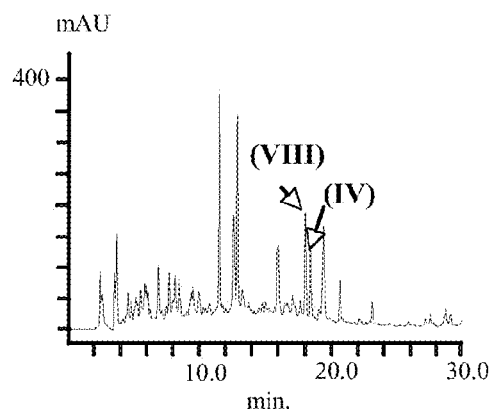
Figure 4C:
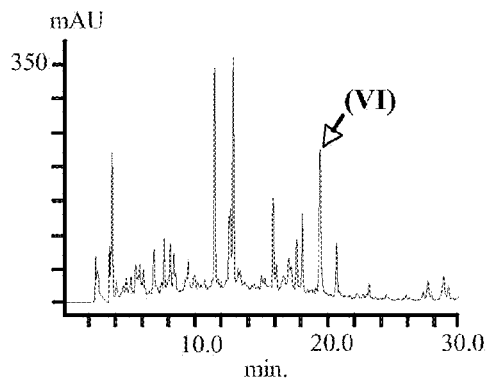
Figure 4D:
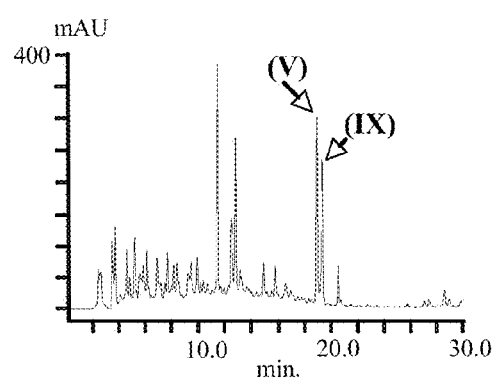
Figure 5:
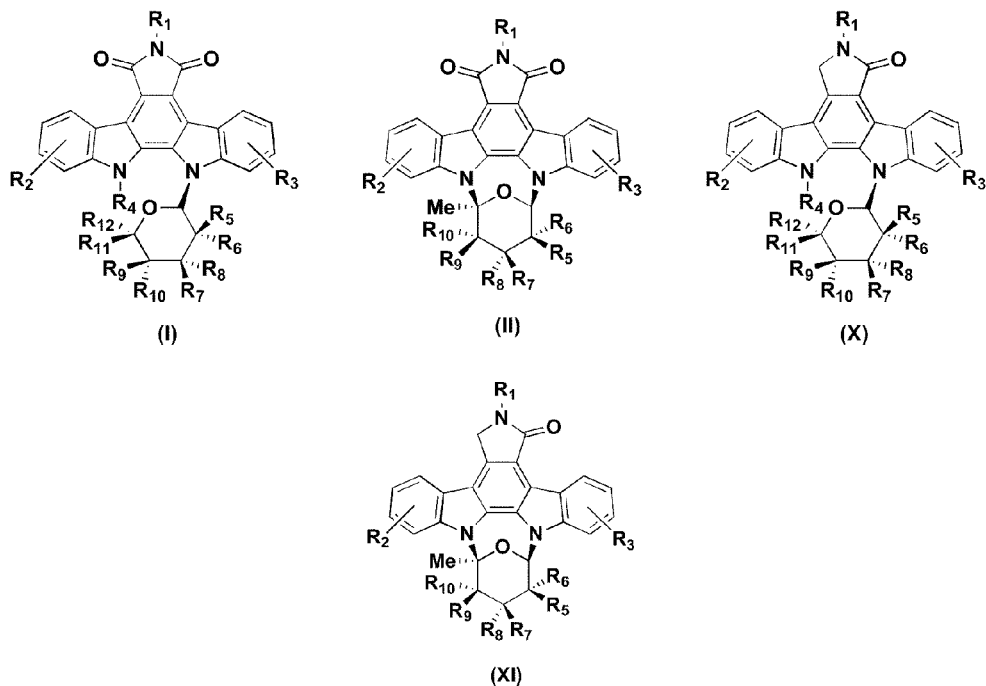
FIG. 5. Chemical structures of [formula (III)], [formula (IV)], [formula (V)], [formula (VI)], [formula (VII)], [formula (VIII)], [formula (IX)], [formula (XII)], [formula (XIII)], [formula (XIV)], [formula (XV)], [formula (XVI)], [formula (XVII)] and [formula (XVIII)].

In this way, the following compounds were obtained (FIG. 4). From *S. albus* 16GNT(pRHAM): 1 mg of $N^{13}$-1'-β-L-rhamnosylarcyriaflavin [formula (III)] and 1.2 mg of $N^{12}$-5' (S)—$N^{13}$-1'-(R)-L-rhamnosylarcyriaflavin [formula (VII)]. From *S. albus* 16GNT(pLN2): 2.1 mg of $N^{12}$-5'(S)—$N^{13}$-1'-(R)-L-olivosylarcyriaflavin [formula (VIII)] and 1.2 mg of $N^{13}$-1'-β-L-olivosylarcyriaflavin [formula (IV)]. From *S. albus* 16GNT(pLNR): 0.8 mg of $N^{13}$-1'-R-D-olivosylarcyriaflavin [formula (VI)]. From *S. albus* 16GNT(pLNBIV): 1.6 mg of $N^{13}$-1'-β-L-digitoxosylarcyriaflavin [formula (V)] and 1.1 mg of $N^{12}$-5'(S)—$N^{13}$-1'-(R)-L-digitoxosylarcyriaflavin [formula (IX)].

The compounds of formulas (XII), (XIII), (XIV), (XV), (XVI) and (XVIII) were obtained similarly, described in *Mol. Microbiol.* 2005, 58, 17-27.

EXAMPLE 3

Characterization of the Compounds of Formula (III), (IV), (V), (VI), (VII), (VIII), (IX), and of the Compounds of Formula (XII), (XIII), (XIV), (XV), (XVI) and (XVIII)

The compounds were initially identified by HPLC analysis, comparing the absorption spectrum and analysing the molecular ion mass. The analysis of the extracts of the *S. albus* 16GNT (pRHAM) strain showed two peaks (FIG. 4A) with m/z ions of 472 and 470, respectively, consistent with the presence of L-rhamnose bound to one and to both nitrogen atoms of the indolocarbazole ring, respectively. The chromatogram corresponding to the 16GNT(pLN2) strain also showed two peaks with the spectrum characteristic of indolocarbazole (FIG. 4B), one with m/z ion of 454 and another with m/z ion of 456. These masses are those expected for the incorporation of L-olivose bound to the aglycone through two and one C—N bond, respectively. In the 16GNT(pLNR) strain a single peak was detected (FIG. 4C) with m/z ion of 456 consistent with the D-olivose bound to a single one of the nitrogens of the aglycone indolocarbazole. Lastly, the 16GNT(pLNBIV) strain showed two peaks (FIG. 4D) with m/z ions of 456 and 454 respectively consistent with the L-digitoxose bond through one and two C—N bonds.

The definitive identification was performed by proton Nuclear Magnetic Resonance (NMR). The sample preparation was performed by dissolving 95-160 μg of pure product in 200 μl of acetone-$d_6$ and transferring to a 3 mm NMR tube. The signals of the solvent were used as internal reference. The NMR spectrums were registered at 298K in a Bruker Avance 600 spectrophotometer equipped with a 5 mm TCI cryoprobe. The typical values for 2D experiments were: COSY, 256 and 2048 points in F1 and F2, respectively, 16 transients each; HSQC-edited, 256 and 2048 points in F1 and F2, respectively, 48 transients each; HMBC, 512 and 2048 points in F1 and F2, respectively, 64 transients each. The mixing times for the 1D sel-nOe experiments were 400 ms. The NMR experiments were processing using the Topspin 1.3 programme (Bruker GmbH, Karlsruhe, Germany). Tables 1 to 7 show the data obtained for the compounds of formulas (III), (IV), (V), (VI), (VII), (VIII) and (IX).

The compounds of formulas (XII), (XIII), (XIV), (XV), (XVI) and (XVIII) were characterized in similar fashion, as described in *Mol. Microbiol.* 2005, 58, 17-27.

EXAMPLE 4

Inhibition of Protein Kinases by the Compounds of Formula (III), (IV), (V), (VI), (VII), (VIII), (IX) and the Compounds of Formula (XII), (XIII), (XIV), (XV), (XVI) and (XVIII)

The analysis of kinase activity described here was performed using LabChip (Caliper Life Sciences), specifically the Caliper LC3000 and the EZ Reader II instruments.

The kinase assay used measures the conversion of a fluorescent peptide (substrate) to a phosphorylated product. The reaction mixture, in a microplate well, is introduced by a capillary in a chip where the non-phosphorylated substrate and the phosphorylated product are separated by fluorescence induced by laser. The intensity of the fluorescent signal over time is related to the reaction progress. The phosphorylated product migrates quicker than the non-phosphorylated substrate and the signals of the two forms of the peptide appear as differentiated peaks. The Caliper determines the peak height and calculates the ratio of product to the peak sum (P/(P+S)). This value is used to compare wells with compounds and wells with controls and thus determine the % of inhibition for the given product.

The followings kinases were used for the enzymatic inhibition studies, between brackets the value of the Michaelis-Menten constant, Km, of the ATP (Adenosine triphosphate) for each kinase, in μM: obtained from Carna Biosciences: MAPKAPK2 (4.6), AurA (3.6), AurB (5), PKCζ (3.8), RSK1 (23.3), PRAK (5), Erk1 (33.4), PKD2 (32.1), CK1d (16.3), CHK1 (33), ABL (61.7), FYN (36), LYNa (17), CHK2 (57.8), MET (79.5), LCK (28.5), SRC (38), GSK3β (7.3), Erk2 (62.1), PKACα (1.7), AKT2 (186.1), INSR (871.8), p38a (396.5), AKT1(48), MSK1 (21.2), PKCβ2 (84.8), ROCK2 (3.3), PIM2 (4.9), AMPK (38.6), KDR (164.8), IRAK4 (196.5), SGK1 (121.8), SYK (33.5); obtained from Invitrogen: CDK2 (57.6), BTK (123), HGK (80); obtained from Upstate: MST2 (36.6), PKGα (16), PAK2 (1.9), IGF1R (320), FGFR1 (171), MARK1 (33), CAMK2δ (22.4), c-TAK1 (66), DYRK1a (18.1), CaMK4 (3.9), FLT3 (350), c-Raf (6.2), P70S6K (95).

The compounds were dissolved in 100% DMSO and were diluted at 25 times the final concentration desired for the assay. In the case of the determination of $CI_{50}$, serial dilutions were made to reach eight concentrations and give rise to the inhibition curve. 1 μL of each concentration is transferred, in duplicate to a 384-well microplate. 12 μL of enzymatic buffer is added to each well containing purified kinase (several suppliers as indicated above), 100 mM HEPES, pH 7.5, 1 mM DTT (Calbiochem), 0.002% Brij-35 (Sigma) and also in presence of 10 mM $MgCl_2$ as cofactor, except for INSR and IRAK4 wherein 10 mM $MnCl_2$ is used instead of $MgCl_2$. For the kinases CAMK26 and CAMK4, 1 mM $CaCl_2$ and 6.7 μg/mL of calmodulin are also added. For KDR kinase, 0.05% of the CHAPSO detergent is added. For the c-Raf kinase, 10 mM $MnCl_2$ is added. For PKCβ2 0.02 μg/mL of PS/PMA is added. For PKGα se 10 μM of cGMP (cyclic guanosine monophosphate) is added. The compound and the enzyme are left for 15 minutes preincubation and, then, the following are added to each well: 12 μL of peptide buffer/ATP containing 100 mM HEPES, pH 7.5, 1.5 μM peptide marker with fluorescein (specific for the corresponding kinase), ATP (at concentration $K_M$), and 0.002% Brij-35 to start the reaction.

Generally, the reactions are incubated for 1-1.5 h at ambient temperature to obtain an adequate conversion (15-40%) of the peptide to the phosphorylated product. The reactions were ended by the addition of 45 μL of buffer containing 0 mM EDTA. The microplates were read by the LabChip 3000 using a 12-channel LabChip. The P/(P+S) values were obtained as described above and the CI50 curves were generated using XIfit.

Table 9a has the 0150 data obtained in pairs of compound-kinase selected from the compounds of formula (VII), (VIII), (IX), (XVI), (XVII) and (XVIII) after taking inhibition measurements at 100 nM and 10 nM. Those couples that provide >70% of inhibition at 10 nM were consider for measuring its IC50.

Table 9b shows the percentage of inhibition obtained by compounds of formula (III), (IV), (V), (VI), (XII), (XIII), (XIV) and (XV) when used at concentrations of 100 nM and 10 nM. For example, the activity of the Dyrk1a kinase is inhibited in 87% by the compound of formula (III) and completely by the compound of formula (XII) when used at a concentration of 10 nM.

EXAMPLE 5

Anti-Tumour Activity of the Compounds of Formula (III), (IV), (V), (VI), (VII), (VIII), (IX) and the Compounds of Formula (XII), (XIII), (XIV), (XV), (XVI) and (XVIII)

The compounds generated were tested against a series of cell lines from tumours. It quantitatively determined the cell growth and the viability, using a colorimetric assay type, using the reaction with sulforhodamine B (SRB), according to the technique described by Faircloth et al. (*Journal of Tissue and Culture Methods* 1988, 11, 201-205). The results are shown in Table 5.

96-well microtitre plates are inoculated with cells ($5 \times 10^3$ cells per well) in aliquots of 195 μl of medium, incubating them during 18 h, in a medium without added compound, to allow the cells to adhere to the surface. Next, the compounds to be tested are added, in samples of 5 μl, at a range of concentrations of 10 to $10^{-8}$ μg/ml, dissolved in DMSO/EtOH (0.2% in PS buffer). After 48 h exposure, the anti-tumour effect is measured using the Sulforhodamine B (SRB) technique: the cells are fixed adding 50 μl of cold trifluoroacetic acid (50%) (w/v) and it is incubated for 60 min. at 4° C. The plates are washed with deionized water and dried. 100 μl of SRB solution (0.4% w/v in 1% acetic acid) to each well and it is incubated during 10 min. at ambient temperature. The non-bound SRB is eliminated, washing with 1% acetic acid. The plates are air dried and the bound colorant is dissolved with Tris buffer. The optical densities are read in an automatic plate spectrophotometer reader at a wavelength of 490 nm.

Table 8 shows the results of the $GI_{50}$ (growth inhibition) in μM. For the compounds of formula (III), (IV), (V), (VI), (VII), (VIII), (IX) and the compounds of formula (XII), (XIII), (XIV), (XV), (XVI) and (XVIII).

TABLE 1

| NMR spectrum data for N13-1'-β-L-rhamnosylarcyriaflavin [formula (III)] in acetone-d6. (1H at 600 MHz, 13C at 150 MHz). | | | | |
|---|---|---|---|---|
| Position | $\delta^{13}C$ (ppm) | $\delta^1H$ (ppm) | Multipl. | J (H, H) (Hz) |
| 1 | 110.83 | 7.826 | d | 8.3 |
| 2 | 127.4 | 7.608 | td | 7.5, 1.2 |

TABLE 1-continued

NMR spectrum data for N13-1'-β-L-rhamnosylarcyriaflavin [formula (III)] in acetone-d6. (1H at 600 MHz, 13C at 150 MHz).

| Position | δ¹³C (ppm) | δ¹H (ppm) | Multipl. | J (H, H) (Hz) |
|---|---|---|---|---|
| 3 | 121.17 | 7.402 | td | 7.6, 0.8 |
| 4 | 125.76 | 9.339 | d | 7.6 |
| 4a | 122.72 | — | | |
| 4b | 119.08 | — | | |
| 4c | NO | — | | |
| 5 | NO | — | | |
| 6 | — | 9.871 | s | |
| 7 | NO | — | | |
| 7a | NO | — | | |
| 7b | 117.87 | — | | |
| 7c | 122.46 | — | | |
| 8 | 125.76 | 9.232 | d | 7.9 |
| 9 | 120.88 | 7.328 | td | 7.6, 1.1 |
| 10 | 127.39 | 7.533 | td | 7.5, 1.2 |
| 11 | 111.81 | 7.647 | d | 8.3, 8.4 |
| 12 | — | 11.727 | s | |
| 11a | 141.62 | — | | |
| 12a | NO | — | | |
| 12b | 129.51 | — | | |
| 13a | 142.87 | — | | |
| 1' | 78.5 | 6.629 | d | 9.5 |
| 2' | 68.76 | 4.774 | ddd | 9.9, 6.8, 3.3 |
| 2'OH | — | 4.654 | m | |
| 3' | 73.09 | 4.469 | d | 3.2 |
| 3'OH | — | 4.65 | m | |
| 4' | 72.36 | 4.34 | d | 3.6 |
| 4'OH | — | 5.92 | d | 3.2 |
| 5' | 78.03 | 4.68 | dq | 7.3, 1.3 |
| 5'CH3 | 15.42 | 1.825 | d | 7.3 |

TABLE 2

NMR spectrum data for N13-1'-β-L-olivosylarcyriaflavin [formula (IV)] in acetone-d6. (1H at 600 MHz, 13C at 150 MHz).

| Position | δ¹³C (ppm) | δ¹H (ppm) | Multipl. | J (H, H) (Hz) |
|---|---|---|---|---|
| 1 | 110.22 | 7.783 | d | 8.4 |
| 2 | 128.27 | 7.644 | t | 7.6 |
| 3 | 121.85 | 7.425 | td | 7.3, 0.8 |
| 4 | 126.59 | 9.367 | d | 8 |
| 4a | 122.63 | — | | |
| 4b | 118.59 | — | | |
| 4c | 120.29 | — | | |
| 5 | NO | — | | |
| 6 | — | 9.879 | s | |
| 7 | NO | — | | |
| 7a | 120.29 | — | | |
| 7b | 116.28 | — | | |
| 7c | 122.17 | — | | |
| 8 | 126.21 | 9.234 | d | 8.1 |
| 9 | 121.38 | 7.35 | td | 7.4, 1.1 |
| 10 | 127.86 | 7.54 | td | 7.1, 1.2 |
| 11 | 112.38 | 7.674 | d | 8.4 |
| 12 | — | 11.935 | s | |
| 11a | 141.41 | — | | |
| 12a | 130.16 | — | | |
| 12b | 129.22 | — | | |
| 13a | 140.9 | — | | |
| 1' | 74.61 | 6.926 | dd | 11.6, 3.4 |
| 2'a | 34.54 | 2.979 | ddd | 14.9, 11.9, 3.3 |
| 2'e | 34.54 | 1.98 | ddd | 14.3, 3.1, 2.7 |
| 3' | 69.97 | 4.461 | m | |
| 3'OH | — | 4.86 | m | |
| 4' | 70.3 | 4.072 | m | |
| 4'OH | — | 5.83 | m | |
| 5' | 78.43 | 4.73 | q | 7.5 |
| 5'CH3 | 15.63 | 1.844 | d | 7.2 |

TABLE 3

NMR spectrum data for N13-1'-β-L-digitoxosylarcyriaflavin [formula (V)] in acetone-d6. (1H at 600 MHz, 13C at 150 MHz).

| Position | δ¹³C (ppm) | δ¹H (ppm) | Multipl. | J (H, H) (Hz) |
|---|---|---|---|---|
| 1 | 110.02 | 7.921 | d | 8.7 |
| 2 | 127.44 | 7.601 | td | 7.4, 1.38 |
| 3 | 121.27 | 7.407 | td | 7.5, 0.8 |
| 4 | 125.89 | 9.364 | d | 7.9 |
| 4a | 122.25 | — | | |
| 4b | 118.68 | — | | |
| 4c | 122.42 | — | | |
| 5 | NO | — | | |
| 6 | — | 9.862 | s | |
| 7 | NO | — | | |
| 7a | 122.42 | — | | |
| 7b | 118.05 | — | | |
| 7c | 122.18 | — | | |
| 8 | 125.38 | 9.231 | d | 8 |
| 9 | 120.5 | 7.338 | td | 7.5, 0.8 |
| 10 | 127.25 | 7.535 | dt | 7.4, 1.1 |
| 11 | 112.13 | 7.743 | d | 7.8 |
| 11a | 141.85 | — | | |
| 12 | — | 12.185 | s | |
| 12a | 130.16 | — | | |
| 12b | 128.97 | — | | |
| 13 | — | | | |
| 13a | 140.95 | — | | |
| 1' | 76.95 | 6.793 | dd | 11.7, 3.5 |
| 2'a | 36.11 | 2.704 | dd | 12.5, 11.9 |
| 2'e | 36.11 | 2.196 | ddd | 12.9, 5.0, 3.5 |
| 3' | 65.3 | 4.62 | ddd | 11.5, 5.3, 2.0 |
| 3'OH | — | NO | | |
| 4' | 71.61 | 4.154 | t | 2 |
| 4'OH | — | NO | | |
| 5' | 76.55 | 4.39 | dq | 1.7, 7.2 |
| 5'CH3 | 14.5 | 1.7 | d | 7.2 |

TABLE 4

NMR spectrum data for N13-1'-β-D-olivosylarcyriaflavin [formula (VI)] in acetone-d6. (1H at 600 MHz, 13C at 150 MHz).

| Position | δ¹³C (ppm) | δ¹H (ppm) | Multipl. | J (H, H) (Hz) |
|---|---|---|---|---|
| 1 | 111.2 | 7.985 | d | 8.6 |
| 2 | 127.6 | 7.629 | td | 7.6, 1.0 |
| 3 | 121.78 | 7.432 | td | 7.3, 0.8 |
| 4 | 125.9 | 9.324 | d | 7.8 |
| 4a | 122.95 | — | | |
| 4b | 119.57 | — | | |
| 4c | NO | — | | |
| 5 | NO | — | | |
| 6 | — | 9.957 | s | |
| 7 | NO | — | | |
| 7a | NO | — | | |
| 7b | NO | — | | |
| 7c | 122.91 | — | | |
| 8 | 125.6 | 9.222 | d | 8 |
| 9 | 121.15 | 7.406 | td | 7.6, 0.8 |
| 10 | 127.79 | 7.601 | td | 7.6, 1.2 |
| 11 | 112.07 | 7.809 | d | 8.2 |
| 12 | | 10.927 | s | |
| 11a | 141.09 | — | | |
| 12a | NO | — | | |
| 12b | NO | — | | |
| 13a | 141.39 | — | | |
| 1' | 82.88 | 6.685 | dd | 11.2, 2.7 |
| 2'a | 29.82 | 2.245 | ddd | 13.2, 11.2, 5.2 |
| 2'e | 29.82 | 2.186 | ddd | 13.2, 5.2, 2.8 |
| 3' | 72.03 | 4.102 | m | |
| 3'OH | — | NO | m | |
| 4' | 78.02 | 3.676 | dd | 9.5, 9.1 |
| 4'OH | — | NO | m | |
| 5' | 76.92 | 4.11 | dd | 9.5, 6.1 |
| 5'CH3 | 18.39 | 1.719 | d | 6.1 |

TABLE 5

NMR spectrum data for N12-5'(S)-N13-1'-(R)-L-rhamnosylarcyriaflavin [formula (VII)] in acetone-d6. ($^1$H at 600 MHz, $^{13}$C at 150 MHz).

| Position | δ$^{13}$C (ppm) | δ$^1$H (ppm) | Multipl. | J (H, H) (Hz) |
|---|---|---|---|---|
| 1 | 109.68 | 8.25 | d | 8.3 |
| 2 | 127.87 | 7.659 | td | 7.1, 1.1 |
| 3 | 120.95 | 7.46 | td | 6.8, 0.8 |
| 4 | 126.06 | 9.26 | d | 7.9 |
| 4a | 122.87 | — | | |
| 4b | NO | — | | |
| 4c | NO | — | | |
| 5 | NO | — | | |
| 6 | — | 9.906 | s | |
| 7 | NO | — | | |
| 7a | NO | — | | |
| 7b | NO | — | | |
| 7c | 124.26 | — | | |
| 8 | 126.06 | 9.38 | d | 8.3 |
| 9 | 120.86 | 7.36 | td | 7.8, 0.8 |
| 10 | 126.11 | 7.518 | td | 6.8, 1.5 |
| 11 | 117.49 | 8.21 | d | 8.6 |
| 11a | 142.82 | — | | |
| 12a | NO | — | | |
| 12b | 129.69 | — | | |
| 13a | 139.08 | — | | |
| 1' | 88.27 | 6.726 | d | 1.8 |
| 2' | 72.75 | 4.47 | s | |
| 2'OH | — | 5.299 | m | |
| 3' | 65.91 | 3.872 | dd | 11.1, 2.6 |
| 3'OH | — | 4.118 | m | |
| 4' | 74.42 | 4.661 | dd | 11.1, 3.7 |
| 4'OH | — | 4.956 | m | |
| 5' | 97.62 | — | | |
| 5'CH3 | 29.77 | 2.463 | s | |

TABLE 6

NMR spectrum data for N$^{12}$-5'(S)-N$^{13}$-1'-(R)-L-olivosylarcyriaflavin [formula (VIII)] in acetone-d6. ($^1$H at 600 MHz, $^{13}$C at 150 MHz).

| Position | δ$^{13}$C (ppm) | δ$^1$H (ppm) | Multipl. | J (H, H) (Hz) |
|---|---|---|---|---|
| 1 | 109.55 | 7.711 | d | 8.3 |
| 2 | 127.44 | 7.641 | td | 7.7, 1.1 |
| 3 | 121.27 | 7.447 | td | 7.4, 0.8 |
| 4 | 125.9 | 9.265 | d | 8.3 |
| 4a | 123.07 | — | | |
| 4b | 117.96 | — | | |
| 4c | NO | — | | |
| 5 | NO | — | | |
| 6 | — | 9.894 | s | |
| 7 | NO | — | | |
| 7a | NO | — | | |
| 7b | 117.96 | — | | |
| 7c | 124.45 | — | | |
| 8 | 125.2 | 8.894 | d | 7.9 |
| 9 | 120.76 | 7.354 | t | 7.1 |
| 10 | 126.58 | 7.509 | dt | 8.0, 1.5 |
| 11 | 116.7 | 8.222 | d | 8.7 |
| 11a | 142.53 | — | | |
| 12a | NO | — | | |
| 12b | 129.68 | — | | |
| 13a | 138.6 | — | | |
| 1' | 83.36 | 6.958 | dd | 4.9, 1.5 |
| 2'a | 38.95 | 2.587 | ddd | 13.8, 11.7, 5.0 |
| 2'e | 38.95 | 2.647 | ddd | 13.8, 4.2, 1.5 |
| 3' | 63.22 | 3.85 | ddd | 11.5, 9.8, 4.2 |
| 3'OH | NO | 3.812 | s | |
| 4' | 81.03 | 4.108 | t | 9.8 |
| 4'OH | — | 4.103 | s | |
| 5' | 97.32 | — | | |
| 5'CH3 | 29.38 | 2.463 | s | |

TABLE 7

NMR spectrum data for N$^{12}$-5'(S)-N$^{13}$-1'-(R)-L-digitoxosylarcyriaflavin [formula (IX)] in acetone-d6. ($^1$H at 600 MHz, $^{13}$C at 150 MHz).

| Position | δμ$^{13}$C (ppm) | δ$^1$H (ppm) | Multipl. | J (H, H) (Hz) |
|---|---|---|---|---|
| 1 | 109.31 | 7.65 | d | 8.3 |
| 2 | 127.07 | 7.6 | td | 7.0, 1.3 |
| 3 | 120.93 | 7.402 | td | 7.3, 1.1 |
| 4 | 125.85 | 9.24 | d | 8 |
| 4a | 123.16 | — | | |
| 4b | 116.15 | — | | |
| 4c | NO | — | | |
| 5 | NO | — | | |
| 6 | — | 9.783 | s | |
| 7 | NO | — | | |
| 7a | NO | — | | |
| 7b | 117.55 | — | | |
| 7c | 124.57 | — | | |
| 8 | 125.31 | 9.36 | d | 8.2 |
| 9 | 120.53 | 7.32 | dt | 7.6, 0.8 |
| 10 | 126.35 | 7.48 | dt | 7.9, 1.6 |
| 11 | 116.34 | 8.18 | d | 8.7 |
| 11a | 142.39 | — | | |
| 12a | NO | — | | |
| 12b | 131.21 | — | | |
| 13a | 139.12 | — | | |
| 1' | 80.37 | 6.82 | dd | 5.6, 1.4 |
| 2'a | 34.85 | 2.8 | ddd | 15, 3.0, 5.6 |
| 2'e | 34.85 | 2.7 | ddd | 15.0, 3.4, 1.4 |
| 3' | 65.14 | 4.275 | ddd | 3.0, 3.0, 3.0 |
| 3'OH | — | NO | | |
| 4' | 74.44 | 4305 | d | 3 |
| 4'OH | — | NO | | |
| 5' | | — | | |
| 5'CH3 | 30.37 | 2.404 | s | |

TABLE 8

Assay of the anti-tumour activity of indolocarbazoles against tumour cell lines.

| Cell line (cancer type) | compounds | | | | | | | | |
|---|---|---|---|---|---|---|---|---|---|
| | STP | RBM | III | IV | V | VI | VII | VIII | IX |
| MDA-MB-231 (breast) | 0.013 | — | 4.40 | 14.1 | 4.19 | 2.43 | 1.35 | 7.50 | 8.16 |
| A549 (lung) | 0.008 | 0.76 | 4.18 | 8.79 | 4.41 | 2.21 | 2.04 | 5.73 | 5.51 |
| HT29 (colon) | 0.076 | 1.55 | 2.42 | 8.79 | 6.39 | 2.16 | 2.45 | 11.2 | 8.16 |

TABLE 8-continued

Assay of the anti-tumour activity of indolocarbazoles against tumour cell lines.

| Cell line (cancer type) | STP | RBM | XII | XIII | XIV | XV | XVI | XVII | XVIII |
|---|---|---|---|---|---|---|---|---|---|
| MDA-MB-231 (breast) | 0.013 | — | 1.97 | 1.43 | 2.49 | 3.17 | 0.59 | 1.05 | 1.84 |
| A549 (lung) | 0.008 | 0.76 | 2.84 | 1.56 | 3.40 | 4.98 | 0.61 | 1.02 | 1.96 |
| HT29 (colon) | 0.076 | 1.55 | 2.10 | 1.52 | 3.40 | 3.85 | 0.87 | 1.21 | 1.52 |

The data obtained with STP and RBM are also included as reference. The numerical values make reference to $GI_{50}$ (μM), or the concentration at which the compound tested inhibits 50% of cell growth in comparison with untreated cells. $N^{13}$-1'-β-L-rhamnosylarcyriaflavin [formula (III)], $N^{13}$-1'-β-L-olivosylarcyriaflavin [formula (IV)], $N^{13}$-1'-β-L-digitoxosylarcyriaflavin [formula (V)], $N^{13}$-1'-β-D-olivosylarcyriaflavin [formula (VI)], $N^{12}$-5'(S)-$N^{13}$-1'-(R)-L-rhamnosylarcyriaflavin [formula (VII)], $N^{12}$-5'(S)-$N^{13}$-1'-(R)-L-olivosylarcyriaflavin [formula (VIII)], $N^{12}$-5'(S)-$N^{13}$-1'-(R)-L-digitoxosylarcyriaflavin [formula (IX)], $N^{13}$-1'-β-L-rhamnosyl-k252c [formula (XII)], $N^{13}$-1'-β-L-olivosyl-k252c [formula (XIII)], $N^{13}$-1'-β-L-digitoxosyl-k252c [formula (XIV)], $N^{13}$-1'-β-D-olivosyl-k252c [formula (XV)], $N^{12}$-5'(S)-$N^{13}$-1'-(R)-L-rhamnosyl-k252c [formula (XVI)], $N^{12}$-5'(S)-$N^{13}$-1'-(R)-L-olivosyl-k252c [formula (XVII)] and $N^{12}$-5'(S)-$N^{13}$-1'-(R)-L-digitoxosyl-k252c [formula (XVIII)].

TABLE 9a

Assay of kinase activity of indolocarbazoles of compounds $N^{12}$-5'(S)-$N^{13}$-1'-(R)-L-rhamnosylarcyriaflavin [formula (VII)], $N^{12}$-5'(S)-$N^{13}$-1'-(R)-L-olivosylarcyriaflavin [formula (VIII)], $N^{12}$-5'(S)-$N^{13}$-1'-(R)-L-digitoxosylarcyriaflavin [formula (IX)], $N^{12}$-5'(S)-$N^{13}$-1'-(R)-L-rhamnosyl-k252c [formula (XVI)], $N^{12}$-5'(S)-$N^{13}$-1'-(R)-L-olivosyl-k252c [formula (XVII)] and $N^{12}$-5'(S)-$N^{13}$-1'-(R)-L-digitoxosyl-k252c [formula (XVIII)].

| | VII | VIII | IX | XVI | XVII | XVIII |
|---|---|---|---|---|---|---|
| AurA | >10 | >10 | 6.7 | — | 5.0 | >10 |
| AurB | — | — | 4.5 | — | 6.8 | — |
| Chk1 | 1.0 | 4.9 | — | 2.4 | — | >10 |
| Dyrk1a | 4.0 | — | >10 | — | — | >100 |
| Ftl3 | 0.57 | 0.56 | 0.43 | 0.59 | 0.54 | — |
| FGFR1 | 8.9 | — | >10 | — | >10 | >100 |
| HGK | 0.78 | — | >10 | — | — | >10 |
| Ikkb | 0.17 | <0.03 | >10 | — | — | >100 |
| Jak2 | 0.50 | 0.74 | 1.2 | 0.43 | 0.57 | 0.53 |
| KDR | 3.7 | 0.55 | >10 | — | — | >10 |
| SYK | 1.0 | 1.1 | 2.3 | — | — | >10 |

The numerical values make reference to $CI_{50}$ (nM), or the concentration at which the assay would inhibit 50% of the kinase activity in comparison with control assays. The kinases assayed are AurA, AurB, Chk1, Dyrk1a, Ftl3, FGFR1, HGK, Ikkb, Jak2, KDR and SYK.

TABLE 9b

Assay of kinase activity of indolocarbazoles of compounds $N^{13}$-1'-β-L-rhamnosylarcyriaflavin [formula (III)], $N^{13}$-1'-β-L-olivosylarcyriaflavin [formula (IV)], $N^{13}$-1'-β-L-digitoxosylarcyriaflavin [formula (V)], $N^{13}$-1'-β-D-olivosylarcyriaflavin [formula (VI)], $N^{13}$-1'-β-L-rhamnosyl-k252c [formula (XII)], $N^{13}$-1'-β-L-olivosyl-k252c [formula (XIII)], $N^{13}$-1'-β-L-digitoxosyl-k252c [formula (XIV)], $N^{13}$-1'-β-D-olivosyl-k252c [formula (XV)].

| | III | | IV | | V | | VI | | XII | | XIII | | XIV | | XV | |
|---|---|---|---|---|---|---|---|---|---|---|---|---|---|---|---|---|
| Kinase | 100 nM | 10 nM | 100 nM | 10 nM | 100 nM | 10 nM | 100 nM | 10 nM | 100 nM | 10 nM | 100 nM | 10 nM | 100 nM | 10 nM | 100 nM | 10 nM |
| AmpKa1 | 11 | 1 | 21 | 3 | 28 | 8 | 33 | 5 | 7 | 1 | 10 | −3 | 1 | 2 | 9 | −3 |
| AurA | 5 | 0 | 19 | 4 | 22 | 4 | 13 | 3 | 3 | 2 | 24 | 2 | 5 | 1 | 20 | 3 |
| CamK2a | 3 | −5 | 29 | 36 | 58 | 15 | 46 | 4 | 2 | −6 | 27 | −6 | 26 | −7 | 29 | −6 |
| Chk1 | 15 | −3 | 35 | 5 | 81 | 45 | 50 | 2 | 8 | 2 | 27 | 1 | 46 | 6 | 20 | 4 |
| Dyrk1a | 103 | 87 | 75 | 32 | 87 | 49 | 94 | 62 | 115 | 101 | 89 | 42 | 73 | 15 | 50 | 14 |
| Erk2 | −4 | −6 | −3 | −2 | 0 | −4 | 30 | −1 | −1 | −3 | 3 | −4 | 0 | −4 | −2 | −4 |
| FGFR1 | 4 | 3 | 21 | 3 | 34 | 7 | 25 | 1 | 5 | 1 | 7 | −1 | 5 | 1 | 7 | −2 |
| FGFR3 | −4 | −10 | 3 | −6 | −1 | −6 | −11 | −8 | −1 | −2 | −6 | −4 | −11 | −6 | −13 | −20 |
| FLT3 | 25 | −10 | 81 | 20 | 95 | 63 | 98 | 51 | 35 | −7 | 89 | 34 | 79 | 20 | 106 | 76 |
| GSK3b | 72 | 21 | 69 | 21 | 81 | 42 | 69 | 18 | 8 | 3 | 9 | 2 | 7 | 1 | 0 | 0 |
| HGK | 89 | 30 | 62 | 9 | 90 | 54 | 83 | 35 | 91 | 44 | 76 | 16 | 78 | 20 | 89 | 36 |
| Ikkb | 32 | −10 | 60 | 9 | 76 | 37 | 50 | 7 | 12 | −5 | 33 | −5 | 24 | 27 | 16 | −5 |
| JAK2 | 33 | −3 | 74 | 19 | 65 | 23 | 88 | 42 | 39 | 7 | 79 | 14 | 25 | −4 | 89 | 37 |
| KDR | 21 | −7 | 68 | 21 | 63 | 28 | 40 | 2 | 6 | −1 | 48 | 7 | 16 | 1 | 18 | −4 |
| MST2 | 10 | 2 | 15 | 2 | 54 | 16 | 65 | 13 | 19 | 4 | 33 | 4 | 34 | 7 | 78 | 12 |
| p38a | −1 | 0 | −2 | −2 | −2 | 1 | −1 | −1 | 0 | −1 | −3 | −2 | −2 | −1 | −3 | −1 |
| PDK1 | 46 | −6 | 71 | 7 | 97 | 76 | 76 | 21 | 15 | −10 | 81 | 9 | 94 | 30 | 81 | 3 |
| RSK1 | 20 | 2 | 77 | 14 | 77 | 38 | 74 | 31 | 7 | −4 | 56 | 7 | 22 | −1 | 31 | −1 |
| SGK1 | 13 | 8 | 17 | 9 | 37 | 17 | 27 | 12 | 6 | 7 | 15 | 8 | 14 | 6 | 12 | 9 |
| SYK | −8 | 2 | 35 | 11 | 24 | 13 | 31 | 5 | 10 | 8 | 30 | 12 | 11 | −1 | 29 | 7 |

The numerical values refer to the remaining kinase activity (in %) after the treatment with the compound tested at concentrations of 10 nM and 100 nM. The kinases tested are AmpKa1, AurA, CamK2a, Chk1, Dyrk1a, Erk2, FGRR1, fgfr3, Etl3, GSK3β, HGK, Ikkb, Jak2, KDR, MST2, p38a, PDK1, RKS1 and SGK1.

The invention claimed is:

1. A compound with any of formulas (I) or (II)

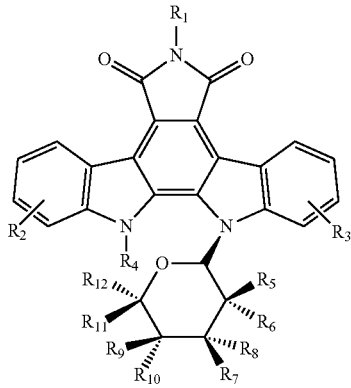
(I)

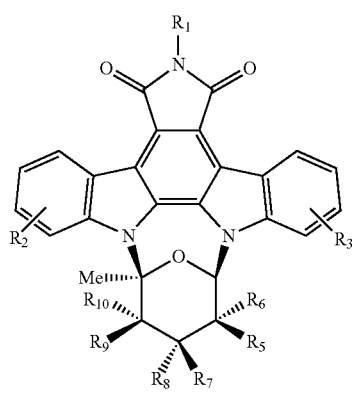
(II)

where $R_1$, $R_2$, $R_3$, $R_4$ and $R_5$ are, hydrogen, $R_6$ is hydroxy or hydrogen, one of $R_7$ and $R_8$ is hydrogen and the other is hydroxy, one of $R_9$ and $R_{10}$ is hydrogen and the other hydroxy, $R_{11}$ is hydrogen or methyl, and $R_{12}$ is hydrogen or methyl.

2. The compound of claim 1, selected from the group consisting of formula (III):

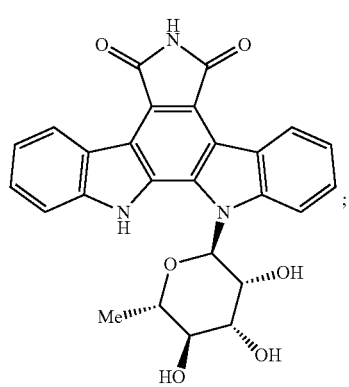
(III)

formula (IV):

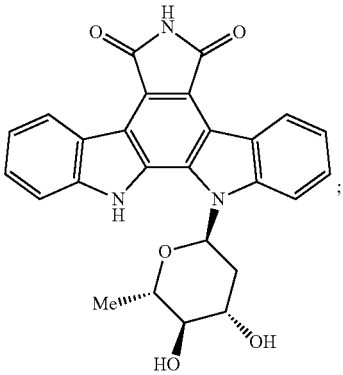
(IV)

formula (V):

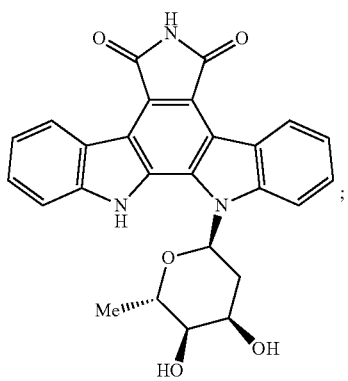
(V)

formula (VI):

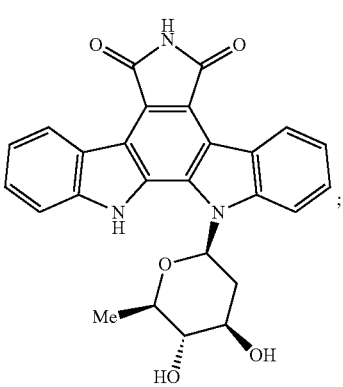
(VI)

formula (VII):

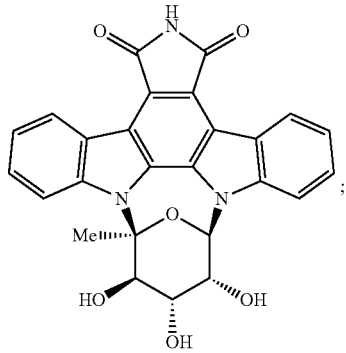

formula (VIII):

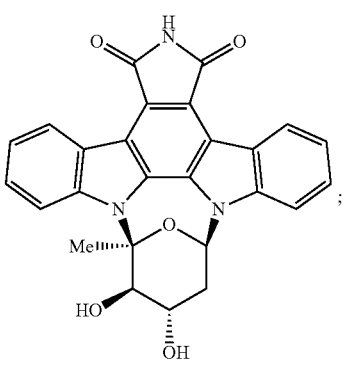

and
formula (IX):

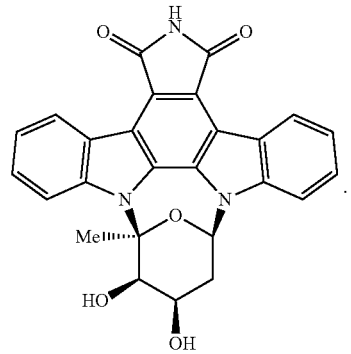

3. Bacterial strains derived from *Streptomyces albus*, characterized in that each one of said strains has additional nucleic acids which encode active enzymes for the biosynthesis of glycosylated indolocarbazoles, these enzymes not being present in *Streptomyces albus*, wherein said strain is selected from the group consisting of *Streptomyces albus* 16GNT (pRHAM), *Streptomyces albus* 16GNT(pLNBIV), *Streptomyces albus* 16GNT(pLN2), and *Streptomyces albus* 16GNT (pLNR).

4. The bacterial strain of claim 3, characterized in that said nucleic acids are the plasmids pKC16GNT and pRHAM, which encode active enzymes for the biosynthesis of the compounds of formula (III):

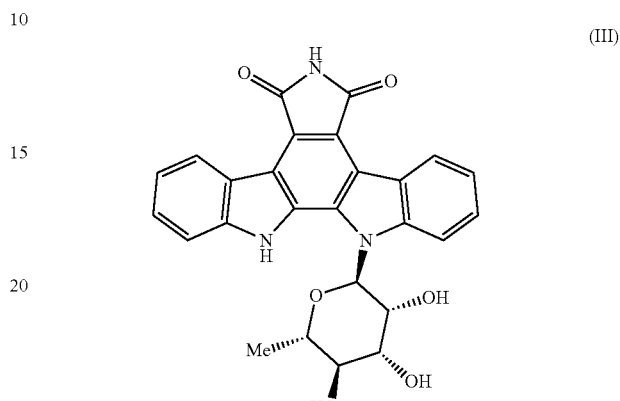

and formula (VII);

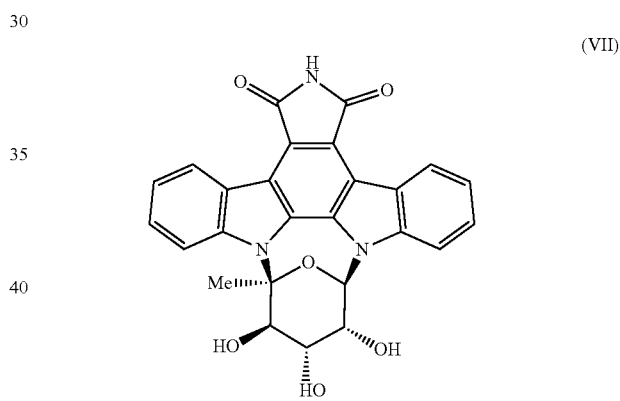

5. The bacterial strain of claim 3, characterized in that said nucleic acids are the plasmids pKC16GNT and pLNBIV, which encode active enzymes for the biosynthesis of the compounds of formula (IV):

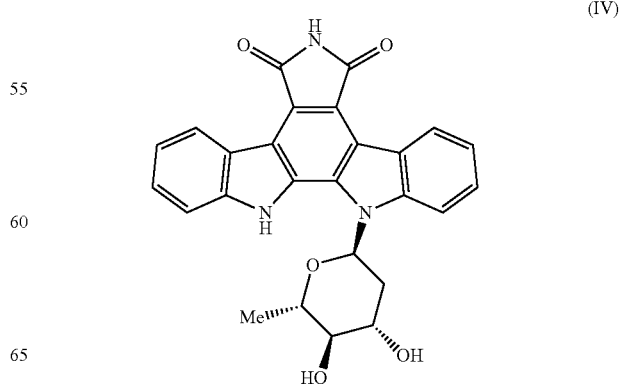

and formula (VIII):

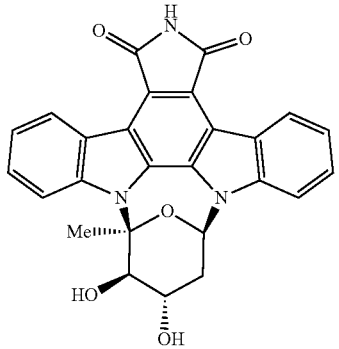
(VIII)

6. The bacterial strain of claim 3, characterized in that said nucleic acids are the plasmids pKC16GNT and pLN2, which encode active enzymes for the biosynthesis of the compounds of formula (V):

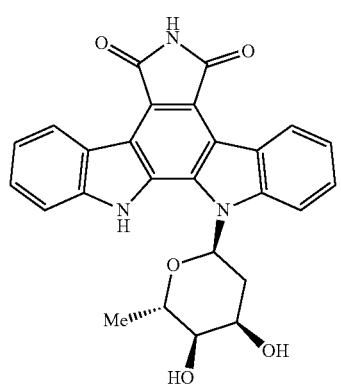
(V)

and formula (IX):

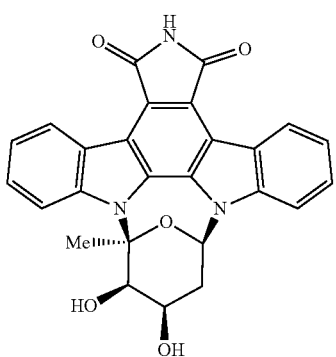
(IX)

7. The bacterial strain of claim 3, characterized in that said nucleic acids are the plasmids pKC16GNT and pLNR, which encode active enzymes for the biosynthesis of the compound of formula (VI):

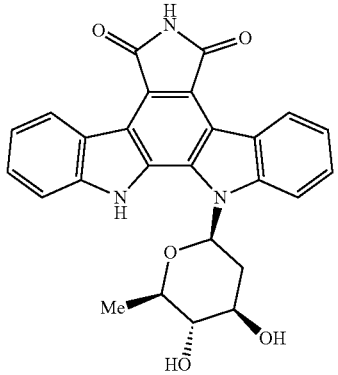
(VI)

8. A method to obtain the bacterial strains of claim 3, which comprises the introduction of a nucleic acid in *Streptomyces albus* or in a strain derived from *Streptomyces albus*.

9. The method of claim 8, where the introduction of a nucleic acid comprises the introduction of: (i) plasmids pKC16GNT and pRHAM in *Streptomyces albus*; (ii) plasmids pKC16GNT and pLNBIV in *Streptomyces albus*; or (iii) plasmids pKC16GNT and pLN2 in *Streptomyces albus*.

10. The method of claim 1, where the introduction of a nucleic acid comprises the introduction of plasmids pKC16GNT and pLNR in *Streptomyces albus*.

11. A method for producing rebeccamycin or staurosporine derivatives according to any of formulas (I) or (II) of claim 1, which comprises:
    a) incubating a bacterial strain to produce a composition including a rebeccamycin or staurosporine derivative according to any of formulas (I) or (II) of claim 1; and
    b) isolating the rebeccamycin or staurosporine derivative from the composition produced in step (a), wherein the bacterial strain is derived from *Streptomyces albus*, characterized in that each one of said strains has additional nucleic acids which encode active enzymes for the biosynthesis of glycosylated indolocarbazoles, these enzymes not being present in *Streptomyces albus*, wherein said strain is selected from the group consisting of *Streptomvces albus* 16GNT(pRHAM), *Streptomvces albus* 16GNT (pLNBIV), *Streptomvces albus* 16GNT(pLN2), and *Streptomvces albus* 16GNT(pLNR.

12. A method according to claim 11, characterized in that the rebeccamycin or staurosporine derivative is selected from the group consisting of the compound of formula (III):

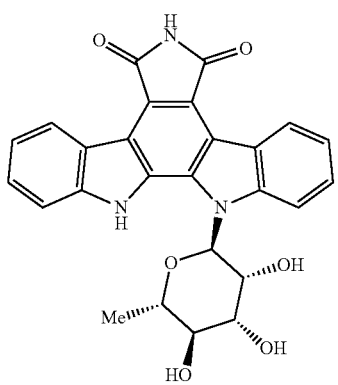
(III)

formula (IV):

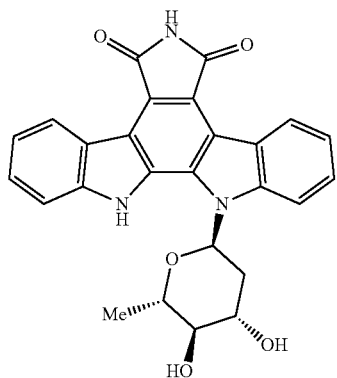

formula (V):

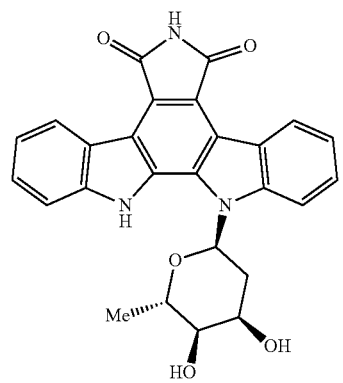

formula (VI):

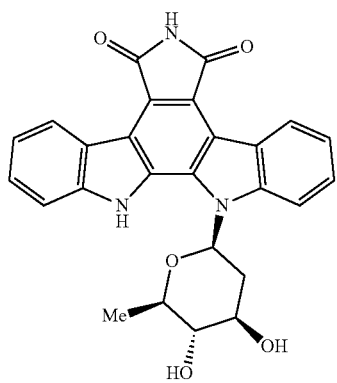

formula (VII):

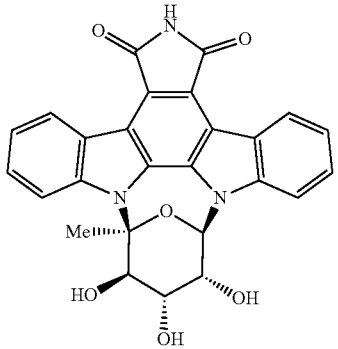

and formula (VIII):

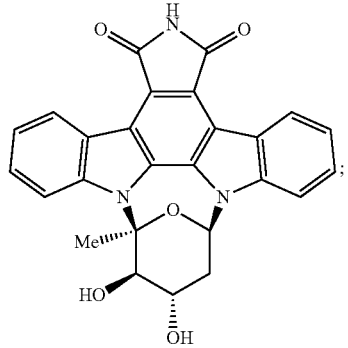

and
formula (IX):

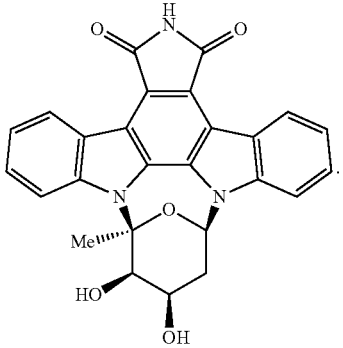

13. A pharmaceutical preparation which comprises a therapeutically effective quantity of a compound of claim 1, or a pharmaceutically effective salt, together with one or more excipients and diluents.

14. A pharmaceutical preparation which comprises a therapeutically effective quantity of a compound of any of formulas (X) or (XI)

(X)

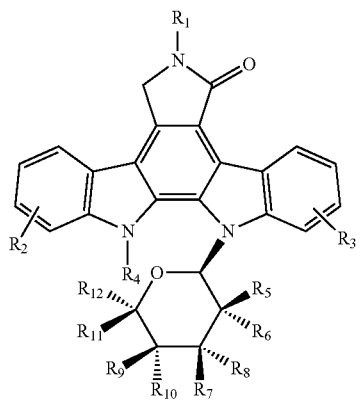

(XI)

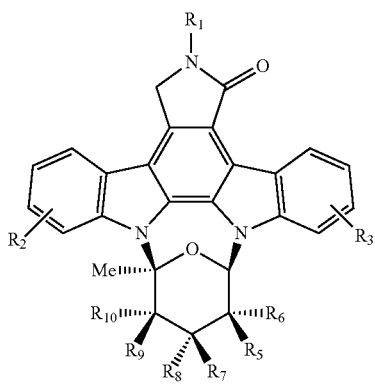

where

R₁, R₂, R₃, R₄, and R₅ are hydrogen,

R₆ is hydroxy or hydrogen, one of R₇ and R₈ is hydrogen and the other is hydroxy, one of R₉ and R₁₀ is hydrogen and the other hydroxy, R₁₁ is hydrogen or methyl, and R₁₂ is hydrogen or methyl.

15. A pharmaceutical preparation in accordance with claim 14, where the compound is selected from the group consisting of formula (XII)

(XII)

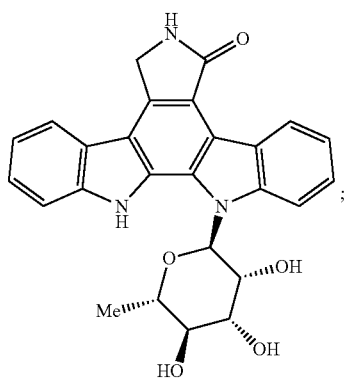

formula (XIII)

(XIII)

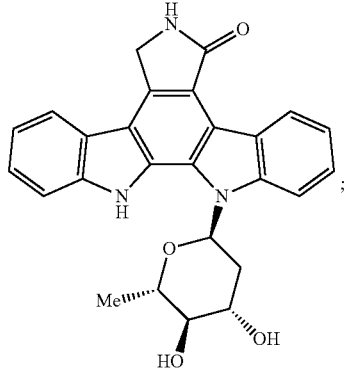

formula (XIV)

(XIV)

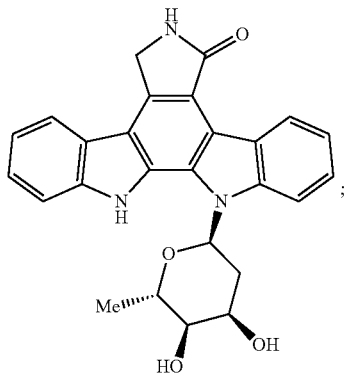

formula (XV)

(XV)

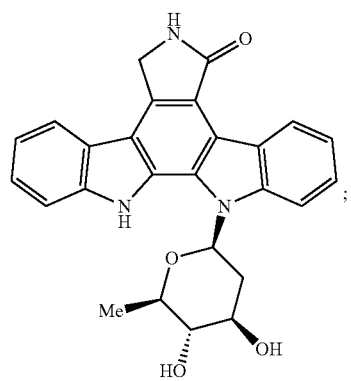

formula (XVI)
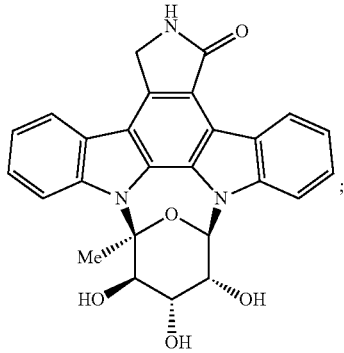
formula (XVII)
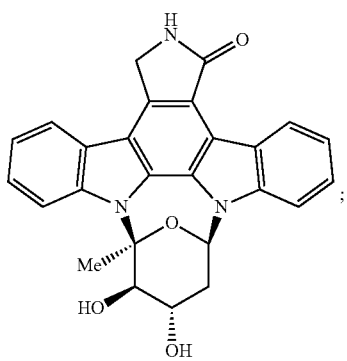
formula (XVIII)
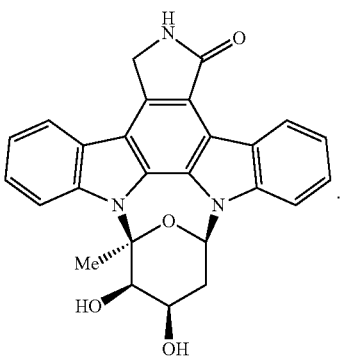
16. A pharmaceutical preparation which comprises a therapeutically effective quantity of a compound with any of formulas (III):
(III)
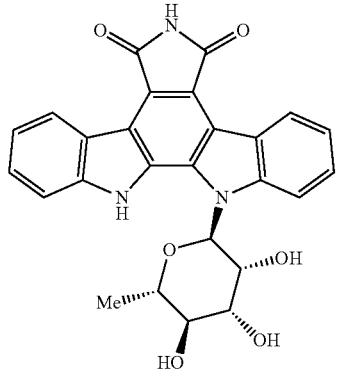
(IV):
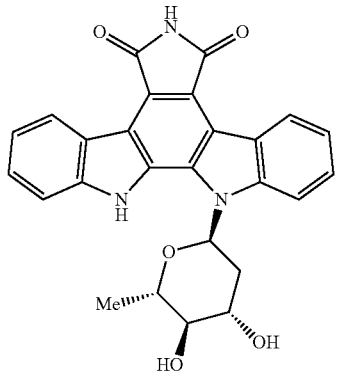
(V):
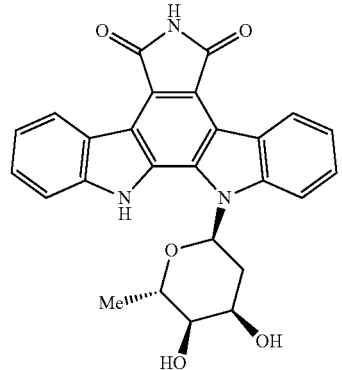

(VI):
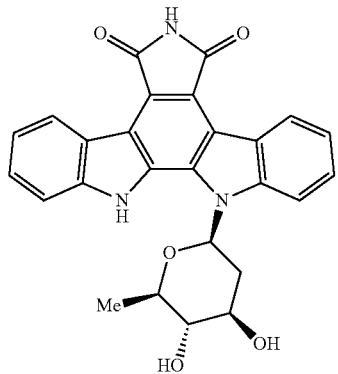
(VII):
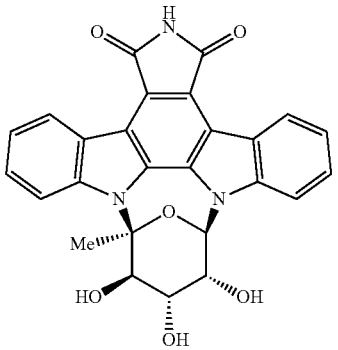
(VIII):
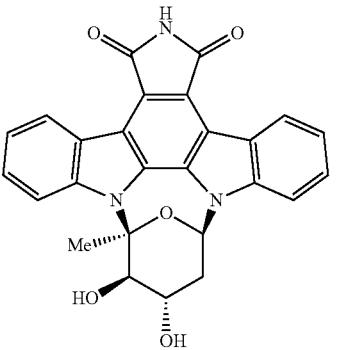
(IX):
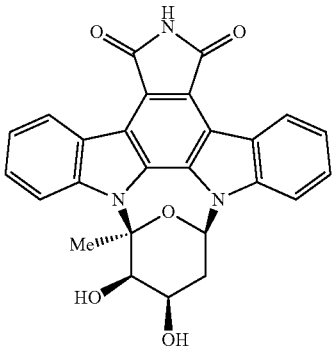
(XII):
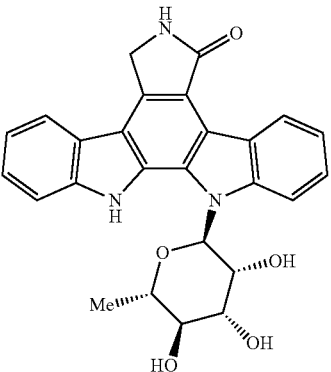
(XIII):
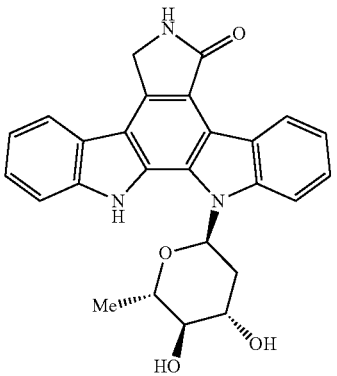

(XIV):
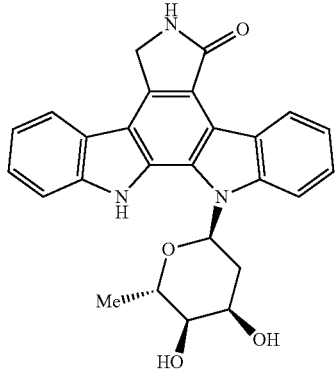
(XV):
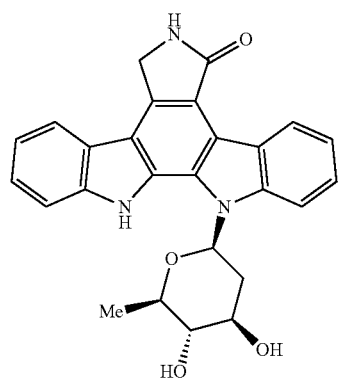
(XVI):
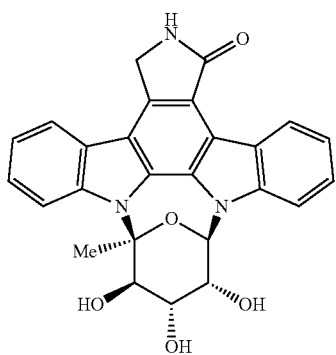
(XVII):
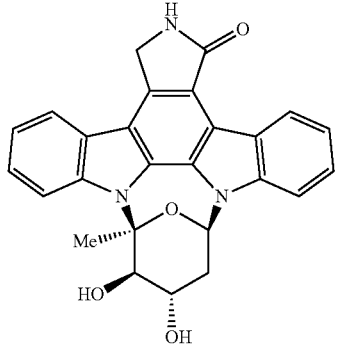
or (XVIII):
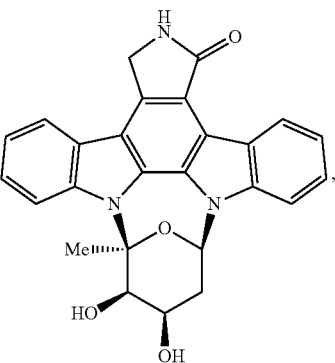
or a pharmaceutically effective salt, together with one or more excipients and diluents.
17. A method of reducing kinase protein activity, said method comprising administering to a subject in need of a reduction in kinase protein activity a therapeutically effective quantity of a compound of any of formulas (III):
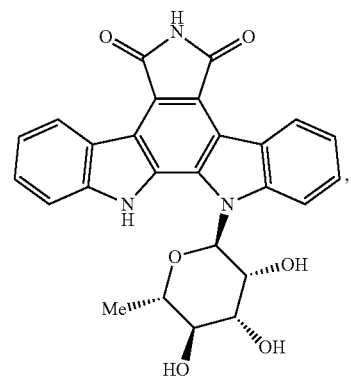

(IV):
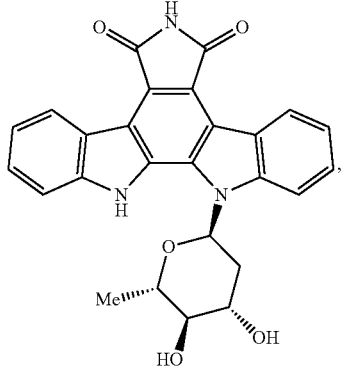
(V):
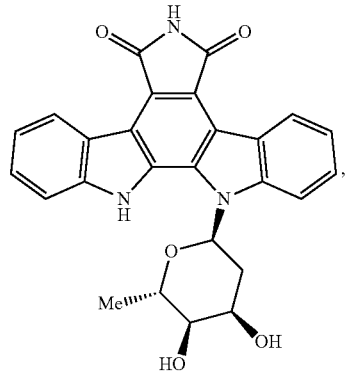
(VI):
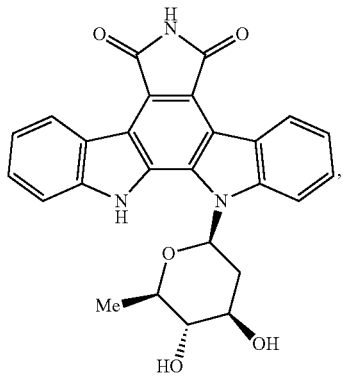
(VII):
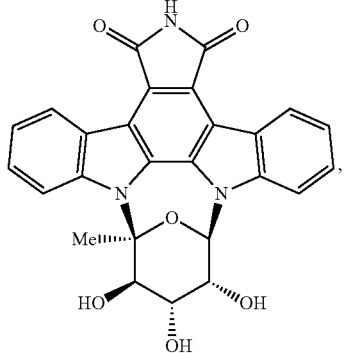
(VIII):
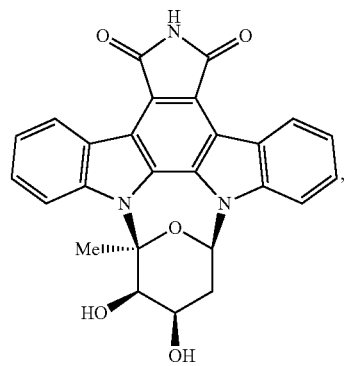
(IX):

(XII):
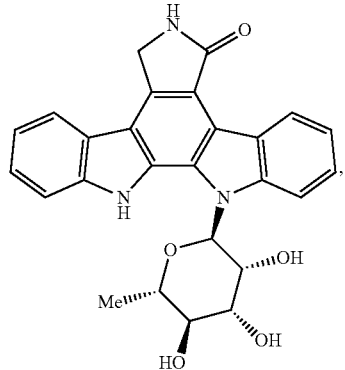
(XIII):
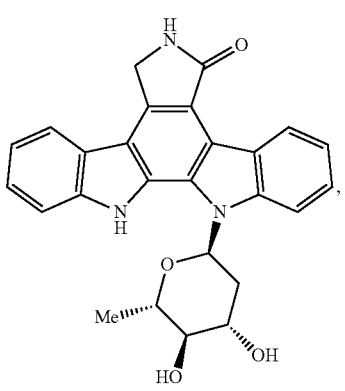
(XIV):
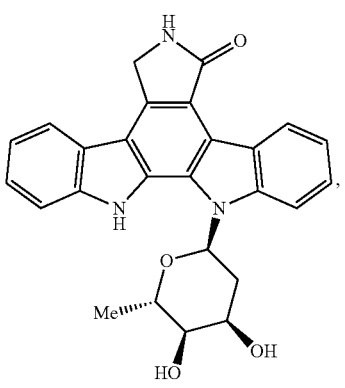
(XV):
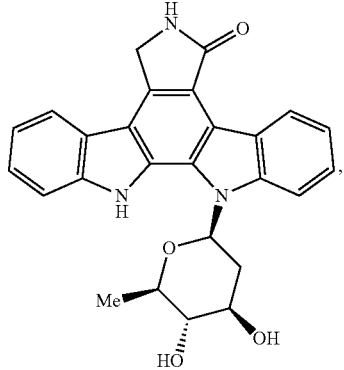
(XVI):
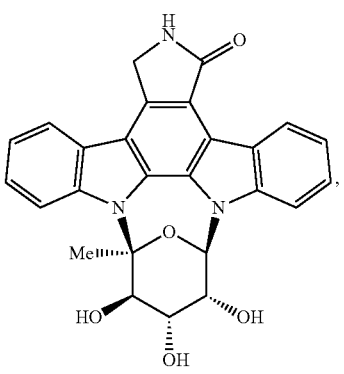
(XVII):
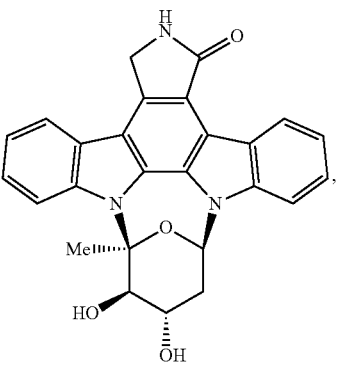

or (XVIII):
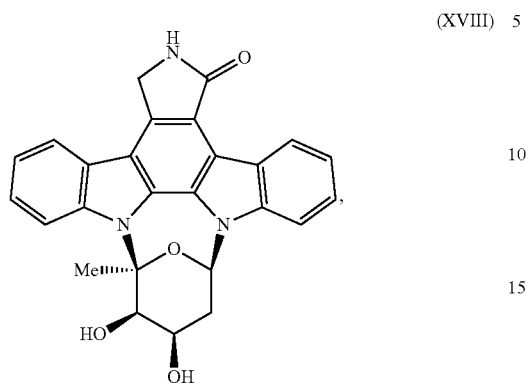
or a pharmaceutically acceptable salt thereof.
18. The method of claim 17, characterized in that the kinase is selected from the group consisting of kinases: AurA, AurB, Chk1, Dyrk1a, Ft13, FGFR1, HGK, Ikkb, Jak2, KDR and SYK.
* * * * *